(12) United States Patent
Clark et al.

(10) Patent No.: US 7,482,356 B2
(45) Date of Patent: Jan. 27, 2009

(54) BICYCLIC PYRAZOLONE CYTOKINE INHIBITORS

(75) Inventors: Michael Philip Clark, Maineville, OH (US); Steven Karl Laughlin, Taylor Mill, KY (US); Adam Golebiowski, Loveland, OH (US); Todd Andrew Brugel, West Chester, OH (US); Mark Sabat, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 495 days.

(21) Appl. No.: 10/983,114

(22) Filed: Nov. 5, 2004

(65) Prior Publication Data

US 2005/0113392 A1 May 26, 2005

Related U.S. Application Data

(60) Provisional application No. 60/518,886, filed on Nov. 10, 2003.

(51) Int. Cl.
*C07D 487/04* (2006.01)
*A61K 31/4162* (2006.01)

(52) U.S. Cl. .................. 514/274; 514/275; 544/315; 544/330

(58) Field of Classification Search .................. 544/315, 544/330; 514/274, 275
See application file for complete search history.

(56) References Cited

U.S. PATENT DOCUMENTS

| 3,449,359 | A | 6/1969 | Testa et al. | |
|---|---|---|---|---|
| 6,472,416 | B1 | 10/2002 | Kolasa et al. | |
| 6,566,357 | B1 * | 5/2003 | Laufersweiler et al. | 514/221 |
| 6,730,668 | B2 * | 5/2004 | Clark et al. | 514/217.06 |
| 6,849,627 | B2 * | 2/2005 | Clark et al. | 514/245 |
| 6,960,593 | B2 * | 11/2005 | Clark et al. | 514/274 |
| 7,087,615 | B2 * | 8/2006 | Clark et al. | 514/269 |

FOREIGN PATENT DOCUMENTS

| CH | 529153 A | 10/1972 |
|---|---|---|
| WO | WO 03/024970 A1 | 3/2003 |
| WO | WO 03/024971 A1 | 3/2003 |
| WO | WO 03/080184 A1 | 10/2003 |
| WO | WO 2004/026878 A1 | 4/2004 |

OTHER PUBLICATIONS

Robinson, Medical Therapy of Inflammatory Bowel Disease for the 21st Century, Eur J Surg 1998; Suppl 582, pp. 90-98.*
Aleman et al., PubMed Abstract (Antivir Ther. 4(2):109-15), 1999.*
Rasmussen, PubMed Abstract (Dan Med Bull. 47(2):94-114), 2000.*
Green et al., PubMed Abstract (Immunol Rev 169:11-22), 1999.*
Van Deventer, PubMed Abstract (Intensive Care Med. 26 Suppl 1:S98-102), 2000.*
Holzheimer, PubMed Abstract (J Chemother. 13 Spec No. 1(1): 159-72), 2001.*
Illei, G. G. et al., "Novel, non-antigen-specific therapeutic approaches to autoimmune/inflammatory diseases", *Current Opinion in Immunology*, 2000, vol. 12, Issue 6, pp. 712-718.
Black, R. A. et al., "Agents that Block TNF-α Synthesis or Acitivity", *Annual Reports in Medicinal Chemistry—32*, Chapter 24, Academic Press, Inc., 1997, pp. 241-250.

* cited by examiner

*Primary Examiner*—Deepak Rao
(74) *Attorney, Agent, or Firm*—Kelly L. McDow

(57) ABSTRACT

The present invention relates to 6,7-dihydro-5H-pyrazolo[1,2α]pyrazol-1-ones which inhibit the extracellular release of inflammatory cytokines, said cytokines responsible for one or more human or higher mammalian disease states. The present invention further relates to compositions comprising said 6,7-dihydro-5H-pyrazolo[1,2α]pyrazol-1-ones and methods for preventing, abating, or otherwise controlling enzymes which are understood to be the active components responsible for the herein described disease states.

29 Claims, No Drawings

BICYCLIC PYRAZOLONE CYTOKINE INHIBITORS

CROSS REFERENCE TO RELATED APPLICATIONS

This application claims priority under Title 35, United States Code 119(e) from Provisional Application Ser. No. 60/518,886, filed Nov. 10, 2003.

FIELD OF THE INVENTION

The present invention relates to 6,7-dihydro-5H-pyrazolo [1,2α]pyrazol-1-ones which inhibit the extracellular release of inflammatory cytokines, said cytokines responsible for one or more human or higher mammalian disease states. The present invention further relates to compositions comprising said 6,7-dihydro-5H-pyrazolo[1,2α]pyrazol-1-ones and methods for preventing, abating, or otherwise controlling enzymes which are understood to be the active components responsible for the herein described disease states.

BACKGROUND OF THE INVENTION

Interleukin-1 (IL-1) and Tumor Necrosis Factor-α (TNF-α) are among the important biological substances known collectively as "cytokines." These molecules are understood to mediate the inflammatory response associated with the immunological recognition of infectious agents.

These pro-inflammatory cytokines are suggested as an important mediators in many disease states or syndromes, inter alia, rheumatoid arthritis, osteoarthritis, inflammatory bowel disease (IBS), septic shock, cardiopulmonary dysfunction, acute respiratory disease, cachexia, and therefore responsible for the progression and manifestation of human disease states.

There is therefore a long felt need for compounds and pharmaceutical compositions which comprise compounds, which can block, abate, control, mitigate, or prevent the release of cytokines from cells which produce them.

SUMMARY OF THE INVENTION

The present invention meets the aforementioned needs in that it has been surprisingly found that certain 3-(2-substituted-pyrimidin-4-yl)-6,7-dihydro-5H-pyrazolo[1,2α]pyrazol-1-ones and derivatives thereof are effective for inhibiting release of inflammatory cytokines, inter alia, interleukin-1 (IL-1) and tumor necrosis factor (TNF) from cells and thereby preventing, abating, or otherwise controlling enzymes which are proposed to be the active components responsible for the herein described disease states.

The present invention encompasses three major aspects each of which have their own separate categories, aspects, iterations, and specific iterative examples. The major aspects of the present invention include:

i) novel compositions of matter which are effective for inhibiting release of inflammatory cytokines, inter alia, interleukin-1 (IL-1) and tumor necrosis factor (TNF) from cells;

ii) compositions or pharmaceutical compositions (matrices) comprising said compositions of matter, and iii) methods for controlling, abating, preventing, or alleviating the symptoms of diseases or disease states which are controllable by administration of said compositions of matter to a human or mammal, whether said composition of matter is administered alone or in a composition or within a pharmaceutical composition (matrix).

The first major aspect of the present invention relates to compounds, including all enantiomeric and diasteriomeric forms and pharmaceutically acceptable salts thereof, said compounds having the formula:

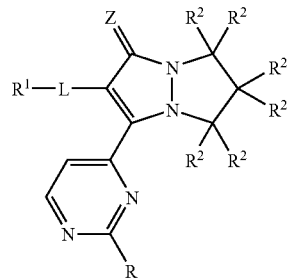

wherein R is:
  a) —O[CH$_2$]$_k$R$^3$; or
  b) —NR$^{4a}$R$^{4b}$;

R$^3$ is substituted or unsubstituted C$_1$-C$_4$ alkyl, substituted or unsubstituted carbocyclic, substituted or unsubstituted heterocyclic, substituted or unsubstituted aryl or alkylenearyl, substituted or unsubstituted heteroaryl or alkyleneheteroaryl; the index k is from 0 to 5;

R$^{4a}$ and R$^{4b}$ are each independently:
  a) hydrogen; or
  b) —[C(R$^{5a}$R$^{5b}$)]$_m$R$^6$;

each R$^{5a}$ and R$^{5b}$ are independently hydrogen, —OR$^7$, —N(R$^7$)$_2$, —CO$_2$R$^7$, —CON(R$^7$)$_2$; C$_1$-C$_4$ linear, branched, or cyclic alkyl, and mixtures thereof; R$^6$ is hydrogen, —OR$^7$, —N(R$^7$)$_2$, —CO$_2$R$^7$, —CON(R$^7$)$_2$; substituted or unsubstituted C$_1$-C$_4$ alkyl, substituted or unsubstituted heterocyclic, substituted or unsubstituted aryl, or substituted or unsubstituted heteroaryl; R$^7$ is hydrogen, a water-soluble cation, C$_1$-C$_4$ alkyl, or substituted or unsubstituted aryl; the index m is from 0 to 5;

R$^1$ is:
  a) substituted or unsubstituted aryl; or
  b) substituted or unsubstituted heteroaryl;

L is a linking group chosen from:
  i) —[C(R$^{12}$)$_2$]$_n$—;
  ii) —[C(R$^{12}$)$_2$]$_n$NR$^{12}$[C(R$^{12}$)$_2$]$_n$—; and
  iii) —[C(R$^{12}$)$_2$]$_n$O[C(R$^{12}$)$_2$]$_n$—;

R$^{12}$ is hydrogen, C$_1$-C$_4$ alkyl, and mixtures thereof; or two R$^{12}$ units can be taken together to form a carbonyl unit; the index n is a unit from 0 to 2;

each R$^2$ unit is independently chosen from:
  a) hydrogen;
  b) —(CH$_2$)$_j$O(CH$_2$)$_j$R$^8$;
  c) —(CH$_2$)$_j$NR$^{9a}$R$^{9b}$;
  d) —(CH$_2$)$_j$CO$_2$R$^{10}$;
  e) —(CH$_2$)$_j$OCO$_2$R$^{10}$
  f) —(CH$_2$)$_j$CON(R$^{10}$)$_2$;
  g) —(CH$_2$)$_j$OCON(R$^{10}$)$_2$;
  h) two R$^2$ units can be taken together to form a carbonyl unit;
  i) and mixtures thereof;

R$^8$, R$^{9a}$, R$^{9b}$, and R$^{10}$ are each independently chosen from hydrogen, C$_1$-C$_4$ alkyl, and mixtures thereof; R$^{9a}$ and R$^{9b}$ can be taken together to form a carbocyclic or heterocyclic ring comprising from 3 to 7 atoms; two R$^{10}$ units can be take together to form a carbocyclic or heterocyclic ring comprising from 3 to 7 atoms; j is an index from 0 to 5; Z is O, S, NR[11], or NOR[11]; R[11] is hydrogen or $C_1$-$C_4$ alkyl.

The second major aspect of the present invention relates to pharmaceutical compositions said compositions comprising:
  a) an effective amount of one or more novel compositions of matter according to the present invention which are effective for inhibiting release of inflammatory cytokines from cells; and
  b) one or more pharmaceutically acceptable excipients.

The third major aspect of the present invention relates to methods of use. As described herein below, the compounds of the present invention are effective in inhibiting release of inflammatory cytokines from cells in humans or higher mammals, and therefore can serve to control, abate, resolve, or otherwise be used to treat one or more diseases or disease states related to the extracellular presence of inflammatory cytokines, for example, osteoarthritis, rheumatoid arthritis, diabetes, and human Immunodeficiency virus (HIV) infection.

The three major aspects of the present invention encompass the discovery that compounds of the present invention, in addition to inhibiting release of inflammatory cytokines from cells, have improved cellular potency and pharmacokinetic properties. This advantage is further exploited in providing a method for controlling diseases which are affected by control or inhibition of inflammatory cytokine inhibitors, said method comprising the step of administering to a human or higher mammal an effective amount of a composition comprising one or more of the inflammatory cytokine inhibitors according to the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The present invention relates to 6,7-dihydro-5H-pyrazolo [1,2α]pyrazol-1-ones which are suitable for mediating, controlling or otherwise inhibiting the extracellular release of certain cytokines, especially inflammatory cytokines, said cytokines playing a role in the stimulation, cause or manifestation of a wide variety of diseases, disease states, or syndromes.

The following chemical hierarchy is used throughout the specification to particularly point out and distinctly claim the units which comprise the compounds of the present invention. The term "hydrocarbyl" stands for any organic molecule, organic functional group, including inorganic atom comprising salts, inter alia, carboxylate salts, quaternary ammonium salts, or for any portion, unit, moiety, and the like, of an organic molecule. Encompassed within the term "hydrocarbyl" are the terms "acyclic" and "cyclic" units which divide hydrocarbyl units into cyclic and non-cyclic families. The family of acyclic units include linear and branched alkyl, alkenyl, alkynyl units and their corresponding connecting units, inter alia, alkylene, alkenylene (—CH═CH—) all of which can be further substituted by the suitable substitutions for hydrogen defined herein below. Encompassed within the family of "cyclic hydrocarbyl" units are the carbocyclic, heterocyclic, aryl, and heteroaryl units, and their corresponding connecting units, inter alia, arylene (e.g., 1,4-phenylene), all of which can be substituted by the suitable substitutions for hydrogen defined herein below. Included within the carbocyclic definition are spirocyclic rings, bicyclic rings, and bridged bicyclic rings, as well as fused rings, inter alia, tetralin. Spirocyclic rings, bicyclic rings, bridged bicyclic rings, and fused rings comprising a heteroatom are divided into categories predicated on the following rules.

For the purposed of the present invention fused ring units, as well as spirocyclic rings, bicyclic rings and the like, which comprise a single heteroatom will be considered to belong to the cyclic family of the heteroatom containing ring. For example, 1,2,3,4-tetrahydroquinoline having the formula:

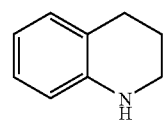

is, for the purposes of the present invention, considered a heterocyclic unit. 6,7-Dihydro-5H -[1]pyridine having the formula:

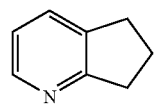

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro -[1,8]naphthyridine having the formula:

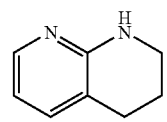

is, for the purposes of the present invention, considered a heteroaryl unit.

The compounds of the present invention comprise linking units. Linking units can be taken together with a substituted or unsubstituted cyclic hydrocarbyl unit to form a single common chemical moiety. For example, a methylene linker and a phenyl unit when taken together is referred to by the artisan of ordinary skill as a benzyl unit, having the formula:

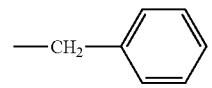

and which is known herein as an "alkylenearyl unit. Likewise a heteroaryl unit taken together with a methylene is defined herein by the term "alkyleneheteroaryl" (e.g. a 2-picolyl unit) having the formula:

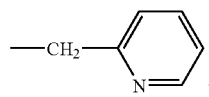

The term "substituted" is used throughout the specification. The term "substituted" is defined herein as "a hydrocarbyl moiety, whether acyclic or cyclic, which has one or more hydrogen atoms replaced by a substituent or several substituents as defined herein below. The units, which substituted for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit."

Although the hydrogen atoms of hydrocarbyl units may be substituted by any unit, the following are non-limiting examples of units which can substitute for a hydrogen atom on a hydrocarbyl unit whether cyclic or acyclic:

i) $-[C(R^{12})_2]_p(CH=CH)_qR^{12}$; wherein p is from 0 to 12; q is from 0 to 12;
ii) $-C(Z)R^{12}$;
iii) $-C(Z)_2R^{12}$;
iv) $-C(Z)CH=CH_2$;
v) $-C(Z)N(R^{12})_2$;
vi) $-C(Z)NR^{12}N(R^{12})_2$;
vii) $-CN$;
viii) $-CNO$;
ix) $-CF_3$, $-CCl_3$, $-CBr_3$;
z) $-N(R^{12})_2$;
xi) $-NR^{12}CN$;
xii) $-NR^{12}C(Z)R^{12}$;
xiii) $-NR^{12}C(Z)N(R^{12})_2$;
xiv) $-NHN(R^{12})_2$;
xv) $-NHOR^{12}$;
xvi) $-NCS$;
xvii) $-NO_2$;
xviii) $-OR^{12}$;
xix) $-OCN$;
xx) $-OCF_3$, $-OCCl_3$, $-OCBr_3$;
xxi) $-F$, $-Cl$, $-Br$, $-I$, and mixtures thereof;
xxii) $-SCN$;
xxiii) $-SO_3M$;
xxiv) $-OSO_3M$;
xxv) $-SO_2N(R^{12})_2$;
xxvi) $-SO_2R^{12}$;
xxvii) $-P(O)H_2$;
xxviii) $-PO_2$;
xxix) $-P(O)(OH)_2$;
xxx) and mixtures thereof;

wherein $R^{12}$ is hydrogen, substituted or unsubstituted $C_1$-$C_{20}$ linear, branched, or cyclic alkyl, $C_6$-$C_{20}$ aryl, $C_7$-$C_{20}$ alkylenearyl, and mixtures thereof; M is hydrogen, or a salt forming cation; Z is $=O$, $=S$, $=NR^{11}$, and mixtures thereof. Suitable salt forming cations include, sodium, lithium, potassium, calcium, magnesium, ammonium, and the like.

The compounds of the present invention have the formula:

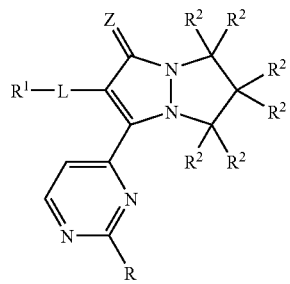

wherein R, $R^1$, and $R^2$ are defined herein below.

R is a substituent at the 2-position of the pyrimidin-4-yl portion of the general scaffold, said R unit is:
a) an ether having the formula $-O[CH_2]_kR^3$; or
b) a primary or secondary amino unit having the formula $-NR^{4a}R^{4b}$;

wherein $R^3$ is substituted or unsubstituted $C_1$-$C_4$ alkyl, substituted or unsubstituted carbocyclic, substituted or unsubstituted heterocyclic, substituted or unsubstituted aryl or alkylenearyl, substituted or unsubstituted heteroaryl or alkyleneheteroaryl; the index k is from 0 to 5.

The following are the various aspects of R units according to the present invention wherein R is an ether having the formula $-O[CH_2]_kR^3$. However, the formulator is not limited to the herein exemplified iterations and examples.

A) R units encompassing ethers having the formula $-OR^3$ (the index k equal to 0) and $R^3$ is substituted or unsubstituted aryl.

i) One iteration of this aspect of R comprises ethers having the formula $-OR^3$ and $R^3$ is substituted or unsubstituted aryl. This iteration includes the following non-limiting example of R: phenoxy, 2-fluorophenoxy, 3-fluorophenoxy, 4-fluorophenoxy, 2,4-difluorophenoxy, 3-trifluoromethylphenoxy, 4-trifluoromethylphenoxy, 2,4-trifluoromethyl phenoxy, and the like.

ii) Another iteration of this aspect of R comprises ethers having the formula $-OR^3$ and $R^3$ is substituted or unsubstituted aryl. This iteration includes the following non-limiting examples: 2-methylphenoxy, 3-methylphenoxy, 4-methylphenoxy, 2,4-dimethylphenoxy, 2-cyanophenoxy, 3-cyanophenoxy, 4-cyanophenoxy, 4-ethylphenoxy, and the like.

iii) A further iteration of this aspect of R comprises ethers having the formula $-OR^3$ and $R^3$ is substituted or unsubstituted aryl. This iteration includes the following non-limiting examples: (2-methyoxy)phenoxy, (3-methoxy)phenoxy, (4-methoxy)phenoxy, 3-[(N-acetyl)amino]phenoxy, 3-benzo[1,3]dioxol-5-yl, and the like.

B) R units encompassing ethers having the formula $-OR^3$ (the index k equal to 0) and $R^3$ is substituted or unsubstituted heteroaryl.

i) A first iteration of this aspect of R comprises ethers having the formula $-OR^3$ and $R^3$ is unsubstituted heteroaryl. This iteration includes the following non-limiting examples: pyrimidin-2-yl, pyrimidin-4-yl, pyridin-2-yl, pyridin-3-yl, pyridin-4-yl, and the like.

ii) A second iteration of this aspect of R comprises ethers having the formula —OR³ and R³ is substituted heteroaryl. This iteration includes the following non-limiting examples: 2-aminopyrimidin-4-yl, and the like.

C) R units encompassing ethers having the formula —OCH₂R³ (the index k equal to 1) and R³ is substituted or unsubstituted aryl.

i) A first iteration of this aspect of R comprises ethers having the formula —OCH₂R³ and R³ is substituted or unsubstituted heteroaryl. This iteration includes the following non-limiting examples: pyrimidin-2-yl, pyrimidin-4-yl, 2-aminopyrimidin-4-yl, 4-aminopyrimidin-6-yl, pyridin-2-yl, pyridin-3-yl, pyridin-4-yl, and the like.

ii) A second iteration of this aspect of R wherein R is an ether having the formula —OCH₂R³ and R³ is substituted or unsubstituted alkyleneheteroaryl. This iteration includes the following non-limiting examples: pyridin-3-ylethyl, (2-methyl-2-pyridin-3-yl)ethyl, and the like.

D) R units encompassing ethers having the formula —OR³ (the index k equal to 1) and R³ is R³ is substituted or unsubstituted C₁-C₄ alkyl.

i) A first iteration of this aspect of R is an ether having the formula —OR³ and R³ is unsubstituted C₁-C₄ linear, branched, or cyclic alkyl. This iteration includes the following non-limiting examples: methyl, ethyl, isopropyl, (S)-1-methypropyl, and the like.

ii) A second iteration of this aspect of R is an ether having the formula —OR³ and R³ is a substituted C₁-C₄ linear, branched, or cyclic alkyl. This iteration includes the following non-limiting examples: 2-methoxyethyl, (S)-1-methy-3-methyoxypropyl, and the like.

The following are the various aspects of R units according to the present invention wherein R is an amine having the formula —NR⁴ᵃR⁴ᵇ, R⁴ᵃ and R⁴ᵇ are each independently:
a) hydrogen; or
b) —[C(R⁵ᵃR⁵ᵇ)]ₘR⁶;

each R⁵ᵃ and R⁵ᵇ are independently hydrogen, or C₁-C₄ linear, branched, —OR⁷, —N(R⁷)₂, —CO₂R⁷, —CON(R⁷)₂; cyclic alkyl, and mixtures thereof; R⁶ is hydrogen, substituted or unsubstituted C₁-C₄ alkyl, substituted or unsubstituted heterocyclic, substituted or unsubstituted aryl, or substituted or unsubstituted heteroaryl; —OR⁷, —N(R⁷)₂, —CO₂R⁷, —CON(R⁷)₂, R⁷ is hydrogen, a water-soluble cation, C₁-C₄ alkyl, or substituted or unsubstituted aryl; the index m is from 0 to 5. However, the formulator is not limited to the herein exemplified iterations and examples.

A) R units encompassing chiral amino groups wherein R⁴ᵃ is hydrogen, R⁵ᵃ is hydrogen and R⁵ᵇ is methyl, said units having the formula:

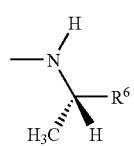

and the indicated stereochemistry.

i) A first iteration of this aspect of R is an amine comprising an R⁶ which is substituted or unsubstituted phenyl. This iteration includes the following non-limiting examples: (S)-1-methyl-1-phenylmethylamino, (S)-1-methyl-1-(4-fluorophenyl)methylamino, (S)-1-methyl-1-(4-methylphenyl)methyl-amino, (S)-1-methyl-1-(4-methoxyphenyl)methylamino, (S)-1-methyl-1-(2-aminophenyl)methylamino, (S)-1-methyl-1-(4-aminophenyl)methylamino, and the like.

ii) A second iteration of this aspect of R is an amine comprising an R⁶ which is substituted or unsubstituted heteroaryl. This iteration includes the following non-limiting examples: (S)-1-methyl-1-(pyridin-2-yl) methylamino, (S)-1-methyl-1-(pyridin-3-yl) methylamino, (S)-1-methyl-1-(pyridin-4-yl) methylamino, (S)-1-methyl-1-(furan-2-yl) methylamino, (S)-1-methyl-1-(3-benzo[1,3]dioxol-5-yl)methylamino, and the like.

iii) A third iteration of this aspect of R is an amine comprising an R⁶ which is C₁-C₄ substituted or unsubstituted alkyl. This iteration includes the following non-limiting examples: (S)-1-methylpropylamino, (S)-1-methyl-2-(methoxy)ethylamino.

B) R units encompassing chiral amino groups wherein R⁴ᵃ is hydrogen, R⁵ᵃ and R⁵ᵇ are each C₁-C₄ alkyl, said units having the formula:

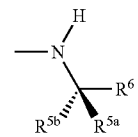

and the indicated stereochemistry when R⁵ᵃ, R⁵ᵇ and R⁶ are not the same.

i) A first iteration of this aspect of R is an amine which does not have a chiral center, non-limiting examples of which includes 1,1-dimethylethylamine, 1,1-dimethylbenzylamine and the like.

ii) A second iteration of this aspect of R is an amine comprising an R⁶ which is substituted or unsubstituted C₁-C₄ alkyl. This iteration includes the following non-limiting examples: (S)-1-methyl-2-hydroxy-2-methylpropylamine, (S)-1-methyl-2-hydroxy-2-methylbutylamine, and the like.

C) R units encompassing alkylenearyl amines wherein R⁴ᵃ is hydrogen, both R⁵ᵃ and R⁵ᵇ of R⁴ᵇ are hydrogen, R⁶ is substituted or unsubstituted aryl, said unit having the formula:

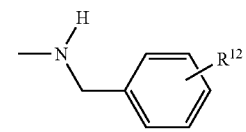

wherein R¹² is hydrogen or a "substituted unit" as defined herein above.

i) A first iteration of this aspect comprises the following non-limiting examples of R units: benzylamino, (2-aminophenyl)methylamino; (4-fluorophenyl)methylamino, (4-methoxyphenyl)methylamino; (4-propanesulfonylphenyl)methylamino; and the like.

ii) A second iteration of this aspect comprises the following non-limiting examples of R units: (2-methylphenyl)methylamino; (3-methylphenyl)-methylamino; (4-methylphenyl)methylamino; and the like.

D) R units encompassing amines wherein $R^{4a}$ is hydrogen, $R^{4b}$ comprises $R^{5a}$ equal to hydrogen and $R^{5b}$ equal to —$CO_2R^7$ or —$CON(R^7)_2$; said unit having the formula:

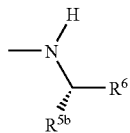

i) A first iteration of this aspect of R is an amine comprising an $R^6$ which is substituted or unsubstituted phenyl. This iteration includes the following non-limiting examples:

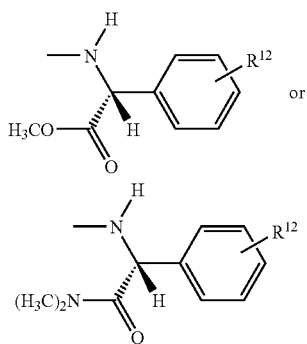

wherein $R^{11}$ is hydrogen or a "substitute" as defined herein above.

ii) A second iteration of this aspect of R is an amine comprising an $R^6$ which is substituted or unsubstituted alkyl. This iteration includes the following non-limiting examples:

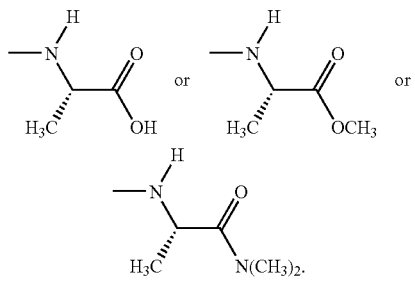

$R^1$ units are selected from:
a) substituted or unsubstituted aryl; or
b) substituted or unsubstituted heteroaryl.

The first aspect of $R^1$ units encompasses halogen substituted phenyl units, non-limiting examples of which include 4-fluorophenyl, 2,4-difluorophenyl, 4-chlorophenyl, and the like.

Each $R^2$ unit is independently selected from the group consisting of:
a) hydrogen;
b) —$(CH_2)_jO(CH_2)_nR^8$;
c) —$(CH_2)_jNR^{9a}R^{9b}$;
d) —$(CH_2)_jCO_2R^{10}$;
e) —$(CH_2)_jOCO_2R^{10}$;
f) —$(CH_2)_jCON(R^{10})_2$;
g) —$(CH_2)_jOCON(R^{10})_2$;
h) two $R^2$ units can be taken together to form a carbonyl unit;
i) and mixtures thereof;

$R^8$, $R^{9a}$, $R^{9b}$, and $R^{10}$ are each independently hydrogen, $C_1$-$C_4$ alkyl, and mixtures thereof; $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5, n is an index from 0 to 5.

L is a linking group chosen from:
i) —$[C(R^{12})_2]_n$—;
ii) —$[C(R^{12})_2]_nNR^{12}[C(R^{12})_2]_n$—; and
iii) —$[C(R^{12})_2]_nO[C(R^{12})_2]_n$—;

$R^{12}$ is hydrogen, $C_1$-$C_4$ alkyl, and mixtures thereof; or two $R^{12}$ units can be taken together to form a carbonyl unit; the index n is a unit from 0 to 2.

The first aspect of L units relates to compounds which comprise L units having the formula:

$$-[C(R^{12})_2]_nO[C(R^{12})_2]_n-$$

the first embodiment of which are compound having the formula:

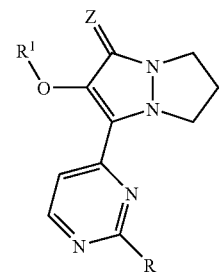

wherein each index n is equal to 0.

The second aspect of the present invention relating to L units comprises compounds having L units with the formula:

$$-[C(R^{12})_2]_n-$$

the first embodiment of this aspect relates to compounds having the formula:

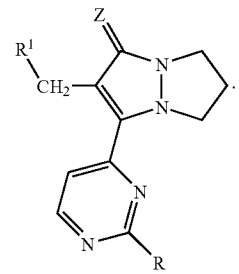

The third aspect of L units relates to compounds which comprise L units having the formula:

$$-[C(R^{12})_2]_nNR^{12}[C(R^{12})_2]_n-$$

the first embodiment of which are compound having the formula:

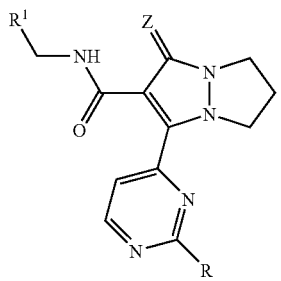

wherein the linking unit is —[CH$_2$]NH[C(O)]—.

The fourth aspect of L units relates to compounds which comprise L units having the formula:

—[C(R$^{12}$)$_2$]— wherein two R$^{12}$ units are taken together to form a carbonyl unit, said compounds having the formula:

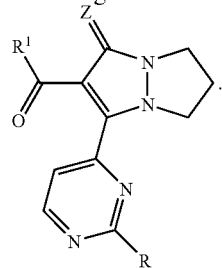

Z is O, S, NR$^{11}$, or NOR$^{11}$; R$^{11}$ is hydrogen or C$_1$-C$_4$ alkyl. The first aspect of the present invention as it relates to Z units, comprises oxygen atoms which provide 2-R$^1$ substituted-3-(2-R-substituted-pyrimidin-4-yl)-6,7-dihydro-5H-pyrazolo [1,2α]pyrazol-1-ones, the second aspect relates to Z units comprising sulfur atoms which provide 2-R$^1$ substituted-3-(2-R-substituted-pyrimidin-4-yl)-6,7-dihydro-5H-pyrazolo [1,2α]pyrazol-1-thiones, and the third aspect of the present invention as it relates to Z units, comprises NR$^{11}$ units thereby providing 2-R$^1$ substituted-3-(2-R-substituted-pyrimidin-4-yl)-6,7-dihydro-5H-pyrazolo[1,2α]pyrazol-1-ylideneamines and derivatives thereof.

The analogs (compounds) of the present invention are arranged into several categories to assist the formulator in applying a rational synthetic strategy for the preparation of analogs which are not expressly exampled herein. The arrangement into categories does not imply increased or decreased efficacy for any of the compositions of matter described herein.

The compounds which comprise Category I of the present invention are to 6,7-dihydro-5H-pyrazolo[1,2α]pyrazol-1-ones having the formula:

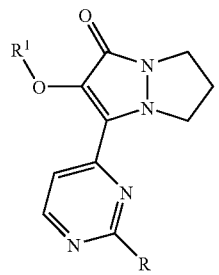

the first aspect of which relates to R units which are substituted alkyl amines, non-limiting examples of which are described herein below in Table I.

TABLE I

| No. | R | R$^1$ |
|---|---|---|
| 1 | 2-methyl-2-hydroxy-1-(S)-methylpropylamine | 2-methylphenyl |
| 2 | 1-(S)-methylbenzylamine | 2-methylphenyl |
| 3 | 2-methoxy-1-(S)-methylethylamine | 2-methylphenyl |
| 4 | 2-methyl-2-cyano-1-(S)-methylpropylamine | 2-methylphenyl |
| 5 | 2-methyl-2-hydroxy-1-(R)-methylpropylamine | 2-methylphenyl |
| 6 | 1-(R)-methylbenzylamine | 2-methylphenyl |
| 7 | 2-methoxy-1-(R)-methylethylamine | 2-methylphenyl |
| 8 | 2-methyl-2-cyano-1-(R)-methylpropylamine | 2-methylphenyl |
| 9 | 2-methyl-2-hydroxy-1-(S)-methylpropylamine | 2-chlorophenyl |
| 10 | 1-(S)-methylbenzylamine | 2-chlorophenyl |
| 11 | 2-methoxy-1-(S)-methylethylamine | 2-chlorophenyl |
| 12 | 2-methyl-2-cyano-1-(S)-methylpropylamine | 2-chlorophenyl |
| 13 | 2-methyl-2-hydroxy-1-(R)-methylpropylamine | 2-chlorophenyl |
| 14 | 1-(R)-methylbenzylamine | 2-chlorophenyl |
| 15 | 2-methoxy-1-(R)-methylethylamine | 2-chlorophenyl |
| 16 | 2-methyl-2-cyano-1-(R)-methylpropylamine | 2-chlorophenyl |
| 17 | 2-methyl-2-hydroxy-1-(S)-methylpropylamine | 4-fluorophenyl |
| 18 | 1-(S)-methylbenzylamine | 4-fluorophenyl |
| 19 | 2-methoxy-1-(S)-methylethylamine | 4-fluorophenyl |
| 20 | 2-methyl-2-cyano-1-(S)-methylpropylamine | 4-fluorophenyl |
| 21 | 2-methyl-2-hydroxy-1-(R)-methylpropylamine | 4-fluorophenyl |
| 22 | 1-(R)-methylbenzylamine | 4-fluorophenyl |
| 23 | 2-methoxy-1-(R)-methylethylamine | 4-fluorophenyl |
| 24 | 2-methyl-2-cyano-1-(R)-methylpropylamine | 4-fluorophenyl |

The compounds which comprise the first aspect of Category I of the present invention can be prepared by the procedure outlined herein below in Scheme I.

Scheme I

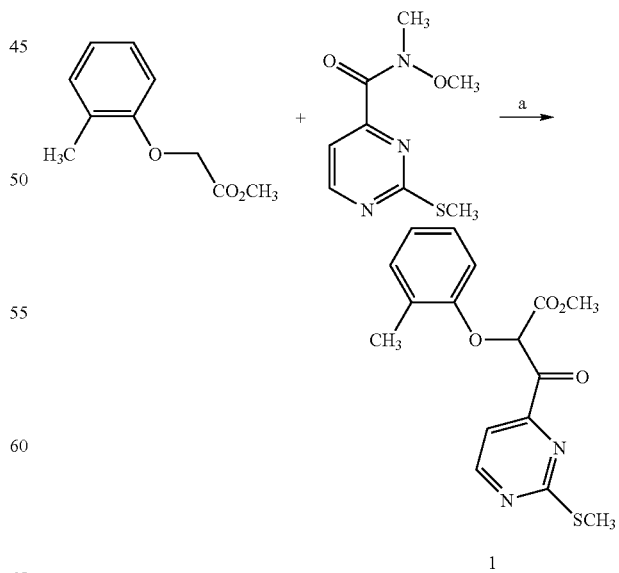

Reagents and conditions: (a) LDA, THF; -78° C. to rt, 1 hr.

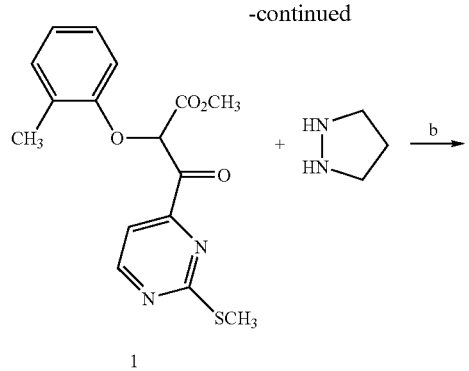

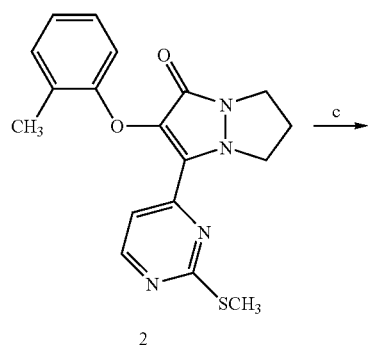

Reagents and conditions: (b) pyridine; reflux, 18 hr.

Reagents and conditions: (c) Oxone, H₂O; rt, 1 hr.

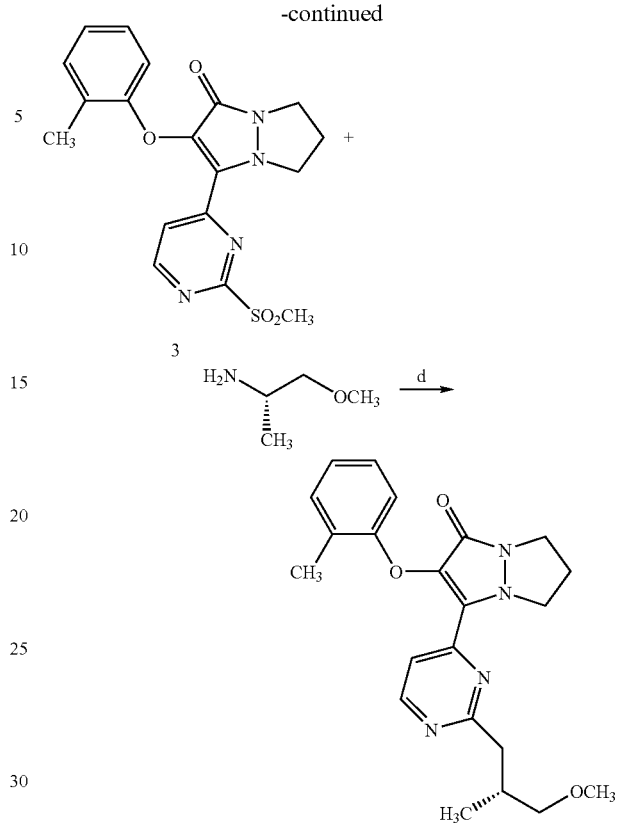

Reagents and conditions: (d) toluene; reflux, 24 hr.

EXAMPLE 1

(S)-3-[2-(2-Methoxy-1-methyl-ethylamino)-pyrimidin-4-yl]-2-o-tolyloxy-6,7-dihydro-5H-pyrazolo[1,2-α]pyrazol-1-one (4)

The starting material 2-methylsulfanyl-pyrimidine-4-carboxylic acid methoxy-methyl-amide can be prepared as follows.

Preparation of 2-methylsulfanyl-pyrimidine-4-carboxylic acid methoxy-methyl-amide: To a slurry of 2-methylsulfanyl-pyrimidine-4-carboxylic acid (10.0 g, 59.2 mmol) in CH₃CN (300 mL) is added in sequence: 1-hydroxybenzotriazole hydrate (9.59 g, 71.0 mmol), 1-(3-dimethylaminopropyl)-3-ethylcarbodiimide hydrochloride (13.6 g, 71.0 mmol), N,O-dimethylhydroxylamine hydrochloride (8.66 g, 88.8 mmol), and triethylamine (Et₃N) (24.9 mL, 178 mmol). The resulting slurry is stirred overnight at ambient temperature. After 16 hours, the reaction mixture is poured into a saturated aqueous solution of sodium bicarbonate (300 mL) and the layers separated. The aqueous layer is extracted with ethyl acetate (3×250 mL). The combined organic layers are washed with brine, dried over sodium sulfate, filtered and concentrated in vacuo and the resulting residue is purified over silica (100% EtOAc) to afford 10.1 g (89% yield) of the desired product as a yellow oil. $^1$H NMR (300 MHz, CDCl₃) δ 8.65 (d, J=4.9 Hz, 1H), 7.15 (br s, 1H), 3.77 (br s, 3H), 3.38 (br s, 3H), 2.61 (s, 3H); MS (ESI) m/z 214 (M+1).

Preparation of 3-(2-Methylsulfanyl-pyrimidin-4-yl)-3-oxo-2-ortho-tolyloxy-propionic acid methyl ester (1): To a cold (−78° C.) solution of lithium diisopropylamide (31.5 mL of 1.8 M solution in THF, 56.6 mmol) in THF (180 mL) is added dropwise a solution of ethyl-(2-methylphenoxy)acetate (10.0 g, 51.5 mmol) in THF (30 mL). After stirring for 1 h at −78° C. a solution of 2-methylsulfanyl-pyrimidine-4-carboxylic acid methoxy-methyl-amide (10.4 g, 48.9 mmol) in THF (30 mL) is added dropwise to the reaction mixture. After stirring 20 min at −78° C., the reaction mixture is warmed to 0° C. and stirred for an additional 30 min. The reaction is quenched by pouring into aqueous saturated $NH_4Cl$. The aqueous phase is extracted with EtOAc (×2). The combined organic phases are dried (MgSO4), filtered and concentrated in vacuo. The crude residue is purified by silica gel chromatography (10% EtOAc/hexanes, followed by 30% EtOAc/hexanes) to afford 2.1 g (32%) of the desired product. $^1H$ NMR (300 MHz, $CDCl_3$) (observed 3:1 mixture of keto: enol tautomers) keto tautomer: δ 8.80 (d, J=4.2 Hz, 1H), 7.57 (d, J=4.8 Hz, 1H), 7.20-7.14 (m, 2H), 6.96 (t, J=7.2 Hz, 1H), 6.85 (d, J=8.1 Hz, 1H), 6.29 (s, 1H), 4.30 (q, J=7.2 Hz, 2H), 2.50 (s, 3H), 2.27 (s, 3H), 1.26 (t, J=7.2 Hz, 3H); $ESI^+$ MS: m/z (rel intensity) 347.1 (100, $M^++H$).

Preparation of 3-(2-Methylsulfanyl-pyrimidin-4-yl)-2-o-tolyloxy-6,7-dihydro-5H-pyrazolo[1,2-a]pyrazol-1-one (2): To a solution of pyrazolidine-bishydrochloride (1.7 g, 11.6 mmol) in pyridine (30 mL) was added 3-(2-Methylsulfanyl-pyrimidin-4-yl)-3-oxo-2-ortho-tolyloxy-propionic acid methyl ester, 1, (2.0 g, 5.78 mmol). The reaction mixture is heated to 110° C. for 18 h. The solvent is removed in vacuo and the resulting residue is purified by silica gel chromatography (10% MeOH/EtOAc, followed by 20% MeOH/EtOAc) to afford 220 mg (10%) of the desired product as a yellow solid. $^1H$ NMR (300 MHz, $CDCl_3$) δ 8.56 (d, J=5.4 Hz, 1H), 7.57 (d, J=5.4 Hz, 1H), 7.23 (d, J=7.5 Hz, 1H), 7.10 (dd, J=7.5, 7.5 Hz, 1H), 6.96 (dd, J=7.5, 7.5 Hz, 1H), 6.82 (d, J=7.5 Hz, 1H), 4.22 (t, J=6.6 Hz, 2H), 4.05 (t, J=6.9 Hz, 2H), 2.72 (dddd, J=6.9, 6.9, 6.9, 6.9 Hz, 2H), 2.62 (s, 3H), 2.48 (s, 3H); $ESI^+$ MS: m/z (rel intensity) 355.0 (100, $M^++H$).

Preparation of 3-(2-Methanesulfonyl-pyrimidin-4-yl)-2-o-tolyloxy-6,7-dihydro-5H-pyrazolo[1,2-a]pyrazol-1-one (3): To a solution of 3-(2-methylsulfanyl-pyrimidin-4-yl)-2-o-tolyloxy-6,7-dihydro-5H-pyrazolo[1,2-a]pyrazol-1-one, 2, (0.20 g, 0.56 mmol) in THF:methanol (6 mL of 1:1 mixture) is added dropwise a solution of Oxone® (potassium peroxymonosulfate) (1.37 g, 2.24 mmol) in $H_2O$ (6 mL). After stirring the reaction for 1 hour at room temperature, the solution is poured into aqueous saturated $NaHCO_3$. The aqueous phase is extracted three times with EtOAc, the organic phases are combined, dried ($MgSO_4$), filtered and concentrated in vacuo to afford the desired product which is used without further purification.

Preparation of (S)-3-[2-(2-Methoxy-1-methyl-ethylamino)-pyrimidin-4-yl]-2-o-tolyloxy-6,7-dihydro-5H-pyrazolo[1,2-a]pyrazol-1-one (4): To a solution of 3-(2-methanesulfonyl-pyrimidin-4-yl)-2-o-tolyloxy-6,7-dihydro-5H-pyrazolo[1,2-a]pyrazol-1-one, 3, (0.11 g, 0.28 mmol) in toluene (4 mL) is added (S)-1-methoxy-2-propylamine (0.10 g, 1.13 mmol). The reaction mixture is heated to 115° C. for 24 h. The solvent is removed in vacuo and the resulting residue is purified by preparative HPLC to afford 52 mg of the desired product as a yellow solid. $^1H$ NMR (300 MHz, $CDCl_3$) δ 8.28 (d, J=5.1 Hz, 1H), 7.22 (d, J=7.2 Hz, 1H), 7.16 (d, J=5.4 Hz, 1H), 7.09 (t, J=7.5 Hz, 1H), 6.97 (t, J=7.5 Hz, 1H), 6.83 (d, J=7.5 Hz, 1H), 4.29-4.21 (m, 1H), 4.17 (t, J=7.2 Hz, 2H), 4.01 (t, J=7.2 Hz, 2H), 3.50 (dddd, J=9.3, 9.3, 4.5, 4.5 Hz, 2H), 3.42 (s, 3H), 2.69 (dt, J=7.2 Hz, 2H), 2.46 (s, 3H), 1.31 (d, J=6.6 Hz, 3H); $ESI^+$ MS: m/z (rel intensity) 396.2 (90, $M^++H$); Anal Calcd for $C_{21}H_{25}N_5O_3$: C, 63.78; H, 6.37; N, 17.71. Found: C, 63.63; H, 6.20; N, 17.05.

The following are non-limiting examples of compounds which comprise the first aspect of Category I.

(S)-3-[2-(2-Hydroxy-1,2-dimethyl-propylamino)-pyrimidin-4-yl]-2-o-tolyloxy-6,7-dihydro-5H-pyrazolo[1,2-a] pyrazol-1-one: $^1H$ NMR (300 MHz, $d_6$-DMSO) δ 8.32 (d, J=5.1 Hz, 1H), 7.24 (d, J=7.2 Hz, 1H), 7.08 (dd, J=7.8, 7.8 Hz, 1H), 6.94 (dd, J=7.2, 7.2 Hz, 1H), 6.87-6.80 (m, 1H), 6.73 (d, J=5.1 Hz, 1H), 4.40 (bd s, 1H), 4.15 (t, J=6.3 Hz, 2H), 3.95 (bd s, 1H), 3.84 (t, J=7.2 Hz, 2H), 3.40-3.35 (m, 1H), 2.62-2.56 (m, 2H), 2.35 (s, 3H), 1.11 (s, 9H). HRMS calcd for $C_{22}H_{28}N_5O_3$ $(M+H)^+$ 410.2192; found 410.2178.

The second aspect of Category I relates to R units which are substituted or unsubstituted heterocyclicamino or heteroarylamino, non-limiting examples of which are described herein below in Table II.

TABLE II

| No. | R | $R^1$ |
|---|---|---|
| 25 | pyran-4-ylamino | 2-methylphenyl |
| 26 | piperidin-4-ylamino | 2-methylphenyl |
| 27 | pyridin-2-ylamino | 2-methylphenyl |
| 28 | pyridin-3-ylamino | 2-methylphenyl |
| 29 | pyridin-4-ylamino | 2-methylphenyl |
| 30 | pyrimidin-2-ylamino | 2-methylphenyl |
| 31 | pyrimidin-4-ylamino | 2-methylphenyl |
| 32 | pyrimidin-5-ylamino | 2-methylphenyl |
| 33 | pyran-4-ylamino | 2-chlorophenyl |
| 34 | piperidin-4-ylamino | 2-chlorophenyl |
| 35 | pyridin-2-ylamino | 2-chlorophenyl |
| 36 | pyridin-3-ylamino | 2-chlorophenyl |
| 37 | pyridin-4-ylamino | 2-chlorophenyl |
| 38 | pyrimidin-2-ylamino | 2-chlorophenyl |
| 39 | pyrimidin-4-ylamino | 2-chlorophenyl |
| 40 | pyrimidin-5-ylamino | 2-chlorophenyl |
| 41 | pyran-4-ylamino | 4-fluorophenyl |
| 42 | piperidin-4-ylamino | 4-fluorophenyl |
| 43 | pyridin-2-ylamino | 4-fluorophenyl |
| 44 | pyridin-3-ylamino | 4-fluorophenyl |
| 45 | pyridin-4-ylamino | 4-fluorophenyl |
| 46 | pyrimidin-2-ylamino | 4-fluorophenyl |
| 47 | pyrimidin-4-ylamino | 4-fluorophenyl |
| 48 | pyrimidin-5-ylamino | 4-fluorophenyl |

The compounds which comprise the second aspect of Category I of the present invention can be prepared by the procedure outlined herein above in Scheme I.

Non-limiting examples of compounds which comprise the second aspect of Category I include:

(S)-3-[2-(Tetrahydro-pyran-4-ylamino)-pyrimidin-4-yl]-2-o-tolyloxy-6,7-dihydro-5H-pyrazolo[1,2-a]pyrazol-1-one: $^1H$ NMR (300 MHz, $CDCl_3$) δ 8.31 (d, J=5.1 Hz, 1H), 7.22 (d, J=7.5 Hz, 1H), 7.14 (d, J=5.1 Hz, 1H), 7.49 (t, J=7.5 Hz, 2H), 7.30-7.22 (m, 4H), 7.09 (t, J=6.6 Hz, 1H), 6.99 (t, J=7.2 Hz, 1H), 6.81 (d, J=5.1 Hz, 1H), 3.95 (t, J=7.2 Hz, 2H), 3.72 (t, J=7.2 Hz, 2H), 2.57-2.47 (m, 4H). $ESI^+$ MS: m/z (rel intensity) 401.2 (100, $M^++H$). Anal Calcd for $C_{22}H_{25}N_5O_3$: C, 64.85; H, 6.18; N, 17.19. Found: C, 64.27; H, 5.94; N, 16.73.

The third aspect of Category I relates to R units which are substituted or unsubstituted arylamino or alkylenearylamino, non-limiting examples of which are described herein below in Table III.

TABLE III

| No. | R | $R^1$ |
|---|---|---|
| 49 | pyran-4-ylamino | 2-methylphenyl |
| 50 | piperidin-4-ylamino | 2-methylphenyl |
| 51 | pyridin-2-ylamino | 2-methylphenyl |
| 52 | pyridin-3-ylamino | 2-methylphenyl |
| 53 | pyridin-4-ylamino | 2-methylphenyl |
| 54 | pyrimidin-2-ylamino | 2-methylphenyl |

TABLE III-continued

| No. | R | R¹ |
|---|---|---|
| 55 | pyrimidin-4-ylamino | 2-methylphenyl |
| 56 | pyrimidin-5-ylamino | 2-methylphenyl |
| 57 | pyran-4-ylamino | 2-chlorophenyl |
| 58 | piperidin-4-ylamino | 2-chlorophenyl |
| 59 | pyridin-2-ylamino | 2-chlorophenyl |
| 60 | pyridin-3-ylamino | 2-chlorophenyl |
| 61 | pyridin-4-ylamino | 2-chlorophenyl |
| 62 | pyrimidin-2-ylamino | 2-chlorophenyl |
| 63 | pyrimidin-4-ylamino | 2-chlorophenyl |
| 64 | pyrimidin-5-ylamino | 2-chlorophenyl |
| 65 | pyran-4-ylamino | 4-fluorophenyl |
| 66 | piperidin-4-ylamino | 4-fluorophenyl |
| 67 | pyridin-2-ylamino | 4-fluorophenyl |
| 68 | pyridin-3-ylamino | 4-fluorophenyl |
| 69 | pyridin-4-ylamino | 4-fluorophenyl |
| 70 | pyrimidin-2-ylamino | 4-fluorophenyl |
| 71 | pyrimidin-4-ylamino | 4-fluorophenyl |
| 72 | pyrimidin-5-ylamino | 4-fluorophenyl |

The compounds which comprise the third aspect of Category I of the present invention can be prepared by the procedure outlined herein above in Scheme I.

Non-limiting examples of compounds which comprise the third aspect of Category I include:

(S)-3-[2-(1-Phenyl-ethylamino)-pyrimidin-4-yl]-2-o-tolyloxy-6,7-dihydro-5H-pyrazolo[1,2-a]pyrazol-1-one: $^1$H NMR (300 MHz, CDCl$_3$) δ 8.31 (d, J=5.1 Hz, 1H), 7.40-7.22 (m, 5H), 7.20 (d, J=7.5 Hz, 1H), 7.12 (d, J=5.1 Hz, 1H), 7.07 (t, J=6.9 Hz, 1H), 6.95 (t, J=7.5 Hz, 1H), 6.80 (d, J=7.8 Hz, 1H), 5.50 (bd s, 1H), 5.12-5.09 (m, 1H), 3.97-3.89 (m, 2H), 3.75-3.60 (m, 1H), 2.44 (s, 3H), 2.60-2.40 (m, 2H), 1.45 (d, J=6.6 Hz, 2H). HRMS calcd for C$_{25}$H$_{26}$N$_5$O$_2$ (M+H)$^+$ 428.2087; found 428.2088.

3-[2-(2,6-Dichloro-phenylamino)-pyrimidin-4-yl]-2-o-tolyloxy-6,7-dihydro-5H-pyrazolo[1,2-a]pyrazol-1-one: $^1$H NMR (300 MHz, CDCl$_3$) δ 8.43 (d, J=5.1 Hz, 1H), 7.46 (d, J=7.8 Hz, 2H), 7.36 (d, J=5.7 Hz, 1H), 7.27-7.21 (m, 2H), 7.12-7.06 (m, 2H), 6.94 (t, J=7.5 Hz, 2H), 6.81 (d, J=8.1 Hz, 1H), 3.98 (t, J=6.9 Hz, 2H), 3.84 (t, J=6.9 Hz, 2H), 2.51 (dddd, J=6.9, 6.9, 6.9, 6.9 Hz, 2H), 2.46 (s, 1H). ESI$^+$ MS: m/z (rel intensity) 468.0 (100, M$^+$+H).

The fourth aspect of Category I relates to R units which are substituted or unsubstituted aryloxy or alkylenearyloxy, non-limiting examples of which are described herein below in Table IV.

TABLE IV

| No. | R | R¹ |
|---|---|---|
| 73 | phenoxy | 2-methylphenyl |
| 74 | 2-chlorophenoxy | 2-methylphenyl |
| 75 | 3-chlorophenoxy | 2-methylphenyl |
| 76 | 2,6-dichlorophenoxy | 2-methylphenyl |
| 77 | 2-methylphenoxy | 2-methylphenyl |
| 78 | 2,6-dimethylphenoxy | 2-methylphenyl |
| 79 | 2-fluorophenoxy | 2-methylphenyl |
| 80 | 2,6-difluorophenoxy | 2-methylphenyl |
| 81 | phenoxy | 2-chlorophenyl |
| 82 | 2-chlorophenoxy | 2-chlorophenyl |
| 83 | 3-chlorophenoxy | 2-chlorophenyl |
| 84 | 2,6-dichlorophenoxy | 2-chlorophenyl |
| 85 | 2-methylphenoxy | 2-chlorophenyl |
| 86 | 2,6-dimethylphenoxy | 2-chlorophenyl |
| 87 | 2-fluorophenoxy | 2-chlorophenyl |
| 88 | 2,6-difluorophenoxy | 2-chlorophenyl |
| 89 | phenoxy | 4-fluorophenyl |
| 90 | 2-chlorophenoxy | 4-fluorophenyl |
| 91 | 3-chlorophenoxy | 4-fluorophenyl |
| 92 | 2,6-dichlorophenoxy | 4-fluorophenyl |

TABLE IV-continued

| No. | R | R¹ |
|---|---|---|
| 93 | 2-methylphenoxy | 4-fluorophenyl |
| 94 | 2,6-dimethylphenoxy | 4-fluorophenyl |
| 95 | 2-fluorophenoxy | 4-fluorophenyl |
| 96 | 2,6-difluorophenoxy | 4-fluorophenyl |

The compounds which comprise the fourth aspect of Category I of the present invention can be prepared by the procedure outlined herein above in Scheme I.

Non-limiting examples of compounds which comprise the fourth aspect of Category I include:

3-(2-Phenoxy-pyrimidin-4-yl)-2-o-tolyloxy-6,7-dihydro-5H-pyrazol-1-one: $^1$H NMR (300 MHz, CDCl$_3$) δ 8.63 (d, J=5.1 Hz, 1H), 7.62 (d, J=5.4 Hz, 1H), 7.49 (t, J=7.5 Hz, 2H), 7.30-7.22 (m, 4H), 7.09 (t, J=7.5 Hz, 1H), 6.96 (t, J=7.2 Hz, 1H), 6.82 (d, J=5.1 Hz, 1H), 5.15 (bd s, NH), 4.13 (t, J=6.9 Hz, 1H), 4.07-4.00 (m, 4H), 3.55 (t, J=11.7 Hz, 2H), 2.69 (dddd, J=6.9 Hz, 2H), 2.46 (s, 3H), 2.05 (d, J=11.7 Hz, 1H), 1.66-1.55 (m, 4H). ESI$^+$ MS: m/z (rel intensity) 408.2 (100, M$^+$+H). Anal Calcd for C$_{23}$H$_{20}$N$_4$O$_3$: C, 68.99; H, 5.03; N, 13.99. Found: C, 69.02; H, 5.01; N, 13.81.

The compounds which comprise Category II of the present invention are to 6,7-dihydro-5H-pyrazolo[1,2α]pyrazol-1-ones having the formula:

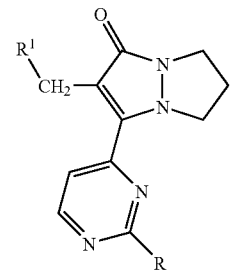

the first aspect of which relates to R units which are substituted or unsubstituted arylamino or alkylenearylamino, non-limiting examples of which are described herein below in Table V.

TABLE V

| No. | R | R¹ |
|---|---|---|
| 97 | pyran-4-ylamino | 2-methylphenyl |
| 98 | piperidin-4-ylamino | 2-methylphenyl |
| 99 | pyridin-2-ylamino | 2-methylphenyl |
| 100 | pyridin-3-ylamino | 2-methylphenyl |
| 101 | pyridin-4-ylamino | 2-methylphenyl |
| 102 | pyrimidin-2-ylamino | 2-methylphenyl |
| 103 | pyrimidin-4-ylamino | 2-methylphenyl |
| 104 | pyrimidin-5-ylamino | 2-methylphenyl |
| 105 | pyran-4-ylamino | 2-chlorophenyl |
| 106 | piperidin-4-ylamino | 2-chlorophenyl |
| 107 | pyridin-2-ylamino | 2-chlorophenyl |
| 108 | pyridin-3-ylamino | 2-chlorophenyl |
| 109 | pyridin-4-ylamino | 2-chlorophenyl |
| 110 | pyrimidin-2-ylamino | 2-chlorophenyl |
| 111 | pyrimidin-4-ylamino | 2-chlorophenyl |

TABLE V-continued

| No. | R | R¹ |
|---|---|---|
| 112 | pyrimidin-5-ylamino | 2-chlorophenyl |
| 113 | pyran-4-ylamino | 4-fluorophenyl |
| 114 | piperidin-4-ylamino | 4-fluorophenyl |
| 115 | pyridin-2-ylamino | 4-fluorophenyl |
| 116 | pyridin-3-ylamino | 4-fluorophenyl |
| 117 | pyridin-4-ylamino | 4-fluorophenyl |
| 118 | pyrimidin-2-ylamino | 4-fluorophenyl |
| 119 | pyrimidin-4-ylamino | 4-fluorophenyl |
| 120 | pyrimidin-5-ylamino | 4-fluorophenyl |

The compounds which comprise the first aspect of Category II of the present invention can be prepared by the procedure outlined herein below in Scheme II.

Scheme II

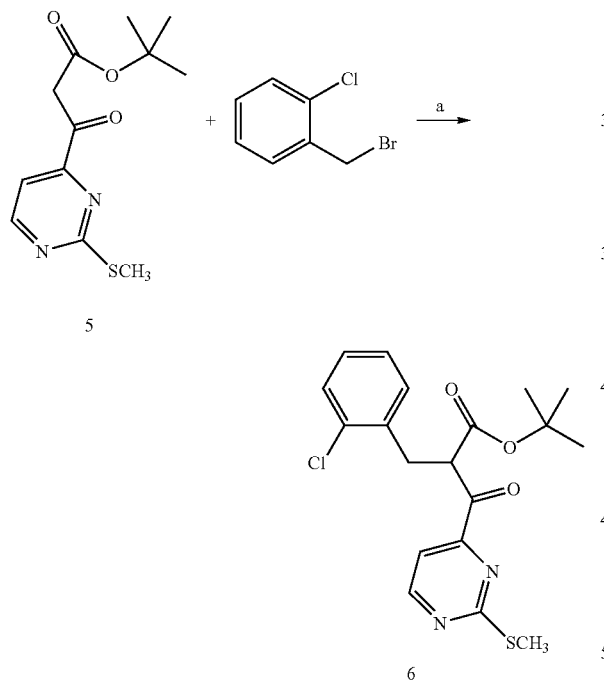

Reagents and conditions: (a) K₂CO₃, 1-crown-6, THF; rt, 20 hr.

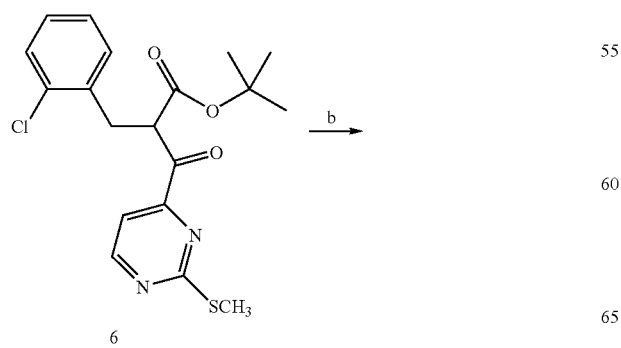

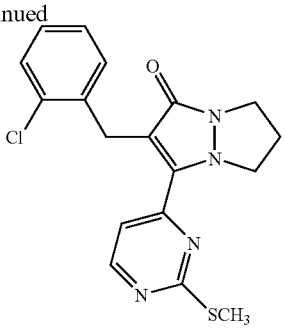

7

Reagents and conditions: (b) pyrazolidine, pyridine; heat, 2 days.

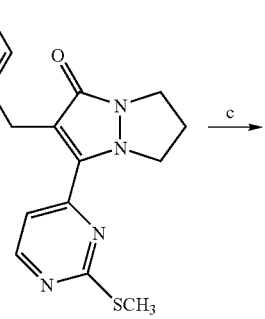

7

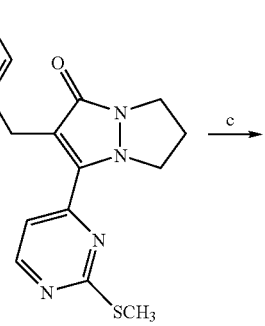

8

Reagents and conditions: (c) Oxone, H₂O; rt, 1.5 hr.

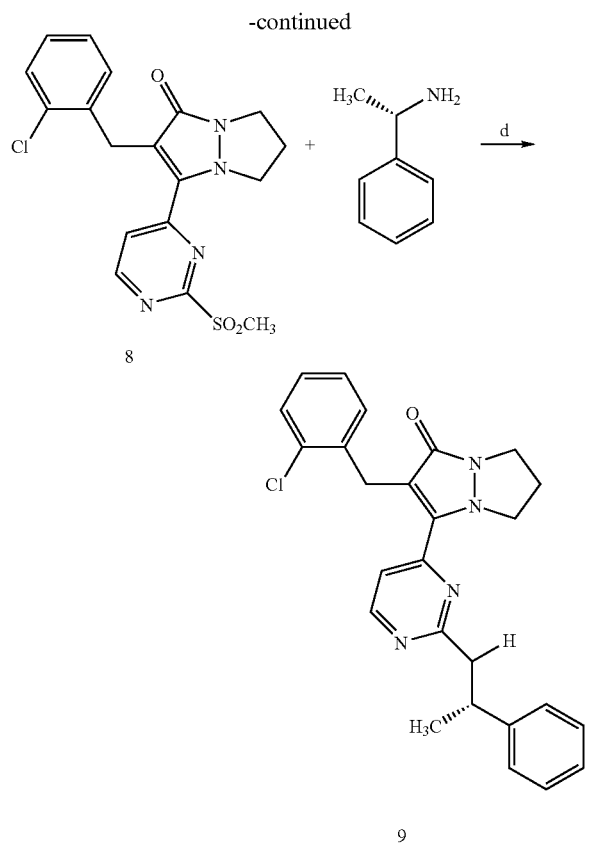

Reagents and conditions: (d) NMP; 90° C. to rt, 1.5 hr.

EXAMPLE 2

(S)-2-(2-Chloro-benzyl)-3-[2-(1-phenyl-ethylamino)-pyrimidin-4-yl]-6,7-dihydro-5H-pyrazolo[1,2-a]pyrazol-1-one (9)

Preparation of 2-(2-chloro-benzyl)-3-(2-methylsulfanyl-pyrimidin-4-yl)-3-oxo-propionic acid tert-butyl ester (6) To a solution of 3-(2-methylsulfanyl-pyrimidin-4-yl)-3-oxo-propionic acid tert-butyl ester, 5, (1.6 g, 6.0 mmol) in THF (15 mL) is added 18-crown-6 (6.3 g, 23.9 mmol) and potassium carbonate (3.3 g, 23.9 mmol). Subsequently, 2-chlorobenzyl bromide (1.2 mL, 9.0 mmol) is added and the mixture is stirred for 20 hours at room temperature. The mixture is diluted with water and ethyl acetate, and the aqueous layer is washed with brine, dried over $MgSO_4$, filtered, and the filtrate is concentrated in vacuo. The crude residue is purified by silica gel chromatography (20% EtOAc/hexanes) to afford 1.9 g (81%) of the desired product: $^1$H NMR (300 MHz, $CDCl_3$) (keto form) δ 8.76 (d, J=5.1 Hz, 1H), 7.52 (dd, J=7.2, 1.8 Hz, 1H), 7.38 (m, 1H), 7.26-7.18 (m, 3H), 4.96 (t, J=7.2 Hz, 1H), 3.52 (dd, J=7.2, 1.8 Hz, 2H), 2.60 (s, 3H), 1.49 (s, 9H); ESI$^+$ MS: m/z 393 M$^+$+H.

Preparation of 2-(2-chloro-benzyl)-3-(2-methylsulfanyl-pyrimidin-4-yl)-6,7-dihydro-5H-pyrazolo[1,2-a]pyrazol-1-one (7): To a solution of 2-(2-chlorobenzyl)-3-(2-methylsulfanyl-pyrimidin-4-yl)-3-oxo-propionic acid tert-butyl ester, 6 (2.0 g, 5.7 mmol)) in pyridine (40 mL) is added pyrazolidine-bishydrochloride (1.2 g, 8.1 mmol). After stirring the reaction for 10 min at room temperature, the mixture i stirred at 90° C. for 2.5 hours and then at 60° C. for 17 hours. The solution i concentrated in vacuo and the resulting curd product is purified over silica (EtOAc followed by 20% MeOH/EtOAc) to afford 460 mg (22%) of the desired product: $^1$H NMR (300 MHz, $CDCl_3$) δ 8.58 (d, J=5.1 Hz, 1H), 7.42-7.2 (m, 4H), 6.96 (d, J=5.1 Hz, 1H), 4.42-4.3 (m, 4H), 4.10 (s, 2H), 2.95-2.75 (m, 2H), 2.58 (s, 3H); ESI$^+$ MS: m/z (rel intensity) 373.0 (100, M$^+$+H).

Preparation of 2-(2-chlorobenzyl)-3-(2-methanesulfonyl-pyrimidin-4-yl)-6,7-dihydro-5H-pyrazolo[1,2-a]pyrazol-1-one (8): To a cold 0° C. solution of 2-(2-chlorobenzyl)-3-(2-methylsulfanyl-pyrimidin-4-yl)-6,7-dihydro-5H-pyrazolo[1,2-a]pyrazol-1-one, 7, (460 mg, 1.23 mmol)) in THF/MeOH (20 mL of 1:1 mixture) is added dropwise a solution of Oxone® (potassium peroxymonosulfate) (3.0 g, 4.9 mmol) in $H_2O$ (15 mL). After stirring the reaction for 1.5 hours at room temperature, the solution is poured into aqueous saturated $NaHCO_3$. The aqueous phase is extracted three times with EtOAc and the combined organic layers are washed with brine, dried ($MgSO_4$), filtered, and concentrated in vacuo to afford 316 mg of the desired product which is used without further purification.

Preparation of (S)-2-(2-chlorobenzyl)-3-[2-(1-phenyl-ethylamino)-pyrimidin-4-yl]-6,7-dihydro-5H-pyrazolo[1,2-a]pyrazol-1-one (9): To a solution of 2-(2-chlorobenzyl)-3-(2-methanesulfonyl-pyrimidin-4-yl)-6,7-dihydro-5H-pyrazolo[1,2-a]pyrazol-1-one, 8, (0.10 g, 0.26 mmol) in NMP (2 mL) is added alpha-methyl benzyl amine (0.10 mL, 0.78 mmol). After stirring 1.5 hours at 90° C., the reaction mixture is diluted with methanol (to 5 mL) and purified by reversed phase liquid chromatography ($CH_3CN$/water/1% TFA) to afford 27 mg (23%) of the desired product: $^1$H NMR (300 MHz, $CDCl_3$) δ 8.27 (d, J=5.1 Hz, 1H), 7.38-7.12 (m, 9H), 6.52 (d, J=5.1 Hz, 1H), 5.06 (q, br, 1H), 4.07-3.95 (m, 4H), 4.02 (s, 2H), 2.58-2.45 (m, 2H), 1.58 (d, J=7.0 Hz, 3H); ESI$^-$ MS: m/z (rel intensity) 446.0 (100, M$^+$–H).

The following are non-limiting examples of compounds which comprise the first aspect of Category II.

(S)-2-(2-Methyl-benzyl)-3-[2-(1-phenyl-ethylamino)-pyrimidin-4-yl]-6,7-dihydro-5H-pyrazolo[1,2-a]pyrazol-1-one: $^1$H NMR (300 MHz, $CDCl_3$) δ 8.00 (d, J=5.1 Hz, 1H), 7.28-6.90 (m, 8H), 6.78 (d, J=7.2 Hz, 1H), 6.45 (d, J=5.1 Hz, 1H), 4.94 (q, br, 1H), 4.07-3.95 (m, 4H), 4.02 (s, 2H), 2.58-2.45 (m, 2H), 2.26 (s, 3H), 1.56 (d, J=7.2 Hz, 3H); ESI$^+$ MS: m/z (rel intensity) 426.0 (100, M$^+$+H).

(S)-2-(4-Fluorobenzyl)-3-[2-(1-phenyl-ethylamino)-pyrimidin-4-yl]-6,7-dihydro-5H-pyrazolo[1,2-a]pyrazol-1-one: $^1$H NMR (300 MHz, $CDCl_3$) δ 8.16 (d, J=5.1 Hz, 1H), 7.40-7.20 (m, 5H), 7.18-7.02 (m, 2H), 6.84 (dd, J=7.2, 1.8 Hz, 2H), 6.68 (s, J=5.1 Hz, 1H), 4.96 (q, br, 1H), 4.18-4.04 (m, 4H), 2.58-2.45 (m, 2H), 1.58 (d, J=7.2 Hz, 3H); ESI$^-$ MS: m/z (rel intensity) 430.0 (100, M$^+$+H).

2-(2-Chlorobenzyl)-3-[2-(2,6-difluoro-phenylamino)-pyrimidin-4-yl]-6,7-dihydro-5H-pyrazolo[1,2-a]pyrazol-1-one: $^1$H NMR (300 MHz, $CDCl_3$) δ 8.42 (d, J=5.1 Hz, 1H), 7.39-7.14 (m, 7H), 6.72 (d, J=5.1 Hz, 1H), 4.16 (t, J=6.9 Hz, 2H), 4.07 (t, J=6.9 Hz, 2H), 4.03 (s, 2H), 2.67 (dddd, J=6.9, 6.9, 6.9, 6.9 Hz, 2H); ESI$^-$ MS: m/z (rel intensity) 453.8 (100, M$^+$–H).

2-(2-Chloro-benzyl)-3-[2-(2-methoxy-1-methyl-ethylamino)-pyrimidin-4-yl]-6,7-dihydro-5H-pyrazolo[1,2-a]pyrazol-1-one: $^1$H NMR (300 MHz, $CDCl_3$) δ 8.14 (d, J=5.1 Hz, 1H), 7.38 (d, J=5.4 Hz, 1H), 7.18-7.10 (m, 3H), 6.61 (d, J=5.4 Hz, 1H), 4.40-4.23 (m, 5H), 4.07 (s, 2H), 3.45 (d, J=5.4 Hz, 2H), 3.38 (s, 3H), 2.82 (dddd, J=6.9, 6.9, 6.9, 6.9 Hz, 2H); ESI$^-$ MS: m/z (rel intensity) 413.9 (100, M$^+$+H).

The second aspect of Category II relates to R units which are substituted or unsubstituted substituted alkyl amines, non-limiting examples of which are described herein below in Table VI.

TABLE VI

| No. | R | R¹ |
|---|---|---|
| 121 | 2-methyl-2-hydroxy-1-(S)-methylpropylamine | 2-methylphenyl |
| 122 | 1-(S)-methylbenzylamine | 2-methylphenyl |
| 123 | 2-methoxy-1-(S)-methylethylamine | 2-methylphenyl |
| 124 | 2-methyl-2-cyano-1-(S)-methylpropylamine | 2-methylphenyl |
| 125 | 2-methyl-2-hydroxy-1-(R)-methylpropylamine | 2-methylphenyl |
| 126 | 1-(R)-methylbenzylamine | 2-methylphenyl |
| 127 | 2-methoxy-1-(R)-methylethylamine | 2-methylphenyl |
| 128 | 2-methyl-2-cyano-1-(R)-methylpropylamine | 2-methylphenyl |
| 129 | 2-methyl-2-hydroxy-1-(S)-methylpropylamine | 2-chlorophenyl |
| 130 | 1-(S)-methylbenzylamine | 2-chlorophenyl |
| 131 | 2-methoxy-1-(S)-methylethylamine | 2-chlorophenyl |
| 132 | 2-methyl-2-cyano-1-(S)-methylpropylamine | 2-chlorophenyl |
| 133 | 2-methyl-2-hydroxy-1-(R)-methylpropylamine | 2-chlorophenyl |
| 134 | 1-(R)-methylbenzylamine | 2-chlorophenyl |
| 135 | 2-methoxy-1-(R)-methylethylamine | 2-chlorophenyl |
| 136 | 2-methyl-2-cyano-1-(R)-methylpropylamine | 2-chlorophenyl |
| 137 | 2-methyl-2-hydroxy-1-(S)-methylpropylamine | 4-fluorophenyl |
| 138 | 1-(S)-methylbenzylamine | 4-fluorophenyl |
| 139 | 2-methoxy-1-(S)-methylethylamine | 4-fluorophenyl |
| 140 | 2-methyl-2-cyano-1-(S)-methylpropylamine | 4-fluorophenyl |
| 141 | 2-methyl-2-hydroxy-1-(R)-methylpropylamine | 4-fluorophenyl |
| 142 | 1-(R)-methylbenzylamine | 4-fluorophenyl |
| 143 | 2-methoxy-1-(R)-methylethylamine | 4-fluorophenyl |
| 144 | 2-methyl-2-cyano-1-(R)-methylpropylamine | 4-fluorophenyl |

The compounds which comprise the second aspect of Category II of the present invention can be prepared by the procedure outlined herein below in Scheme II.

Non-limiting examples of compounds which comprise the second aspect of Category II include:

(S)-2-(2-Chloro-benzyl)-3-[2-(2-hydroxy-1,2-dimethyl-propylamino)-pyrimidin-4-yl]-6,7-dihydro-5H-pyrazolo[1,2-a]pyrazol-1-one: $^1$H NMR (300 MHz, CDCl$_3$) δ 8.23 (d, J=5.1 Hz, 1H), 7.39-7.34 (m, 1H), 7.26-7.13 (m, 3H), 8.58 (d, J=5.1 Hz, 1H), 4.15-4.10 (m, 7H), 2.8-2.75 (m, 2H), 1.26 (d, J=9.1 Hz, 6H), 1.20 (d, J=6.8 Hz, 3H); ESI$^-$ MS: m/z (rel intensity) 428.0 (100, M$^+$–H).

(S)-3-[2-(2-Hydroxy-1,2-dimethyl-propylamino)-pyrimidin-4-yl]-2-(2-methyl-benzyl)-6,7-dihydro-5H-pyrazolo[1,2-a]pyrazol-1-one: $^1$H NMR (300 MHz, CDCl$_3$) δ 7.98 (d, J=5.1 Hz, 1H), 7.29-6.98 (m, 3H), 6.85 (d, J=5.1 Hz, 1H), 6.52 (d, J=5.1 Hz, 1H), 4.30-4.10 (m, 4H), 3.99 (q, J=7.2.Hz, 1H), 2.88-2.72 (m, 2H), 2.26 (s, 3H), 1.26-1.15 (m, 9H); ESI$^-$ MS: m/z (rel intensity) 408.0 (100, M$^+$–H).

(S)-2-(4-Fluoro-benzyl)-3-[2-(2-hydroxy-1,2-dimethyl-propylamino)-pyrimidin-4-yl]-6,7-dihydro-5H-pyrazolo[1,2-a]pyrazol-1-one: $^1$H NMR (300 MHz, CDCl$_3$) δ 8.15 (d, J=5.1 Hz, 1H), 7.12-7.05 (m, 2H), 6.88 (dd, J=7.2, 1.8 Hz, 2H), 6.72 (d, J=5.1 Hz, 1H), 4.28-4.06 (m, 4H), 3.88 (s, 2H), 2.82-2.70 (m, 2H), 1.26-1.15 (m, 9H); ESI$^+$ MS: m/z (rel intensity) 412.1 (100, M$^+$+H).

The third aspect of Category II relates to R units which are substituted or unsubstituted heterocyclicamino or heteroarylamino, non-limiting examples of which are described herein below in Table VII.

TABLE VII

| No. | R | R¹ |
|---|---|---|
| 145 | pyran-4-ylamino | 2-methylphenyl |
| 146 | piperidin-4-ylamino | 2-methylphenyl |
| 147 | pyridin-2-ylamino | 2-methylphenyl |
| 148 | pyridin-3-ylamino | 2-methylphenyl |
| 149 | pyridin-4-ylamino | 2-methylphenyl |
| 150 | pyrimidin-2-ylamino | 2-methylphenyl |
| 151 | pyrimidin-4-ylamino | 2-methylphenyl |
| 152 | pyrimidin-5-ylamino | 2-methylphenyl |
| 153 | pyran-4-ylamino | 2-chlorophenyl |
| 154 | piperidin-4-ylamino | 2-chlorophenyl |
| 155 | pyridin-2-ylamino | 2-chlorophenyl |
| 156 | pyridin-3-ylamino | 2-chlorophenyl |
| 157 | pyridin-4-ylamino | 2-chlorophenyl |
| 158 | pyrimidin-2-ylamino | 2-chlorophenyl |
| 159 | pyrimidin-4-ylamino | 2-chlorophenyl |
| 160 | pyrimidin-5-ylamino | 2-chlorophenyl |
| 161 | pyran-4-ylamino | 4-fluorophenyl |
| 162 | piperidin-4-ylamino | 4-fluorophenyl |
| 163 | pyridin-2-ylamino | 4-fluorophenyl |
| 164 | pyridin-3-ylamino | 4-fluorophenyl |
| 165 | pyridin-4-ylamino | 4-fluorophenyl |
| 166 | pyrimidin-2-ylamino | 4-fluorophenyl |
| 167 | pyrimidin-4-ylamino | 4-fluorophenyl |
| 168 | pyrimidin-5-ylamino | 4-fluorophenyl |

The following is an example of the preparation of a compound which comprises the third aspect of Category II.

Preparation of 2-(2-chlorobenzyl)-3-[2-(tetrahydro-pyran-4-ylamino)-pyrimidin-4-yl]-6,7-dihydro-5H-pyrazolo[1,2-a]pyrazol-1-one: To a solution of 2-(2-chloro-benzyl)-3-(2-methanesulfonyl-pyrimidin-4-yl)-6,7-dihydro-5H-pyrazolo[1,2-a]pyrazol-1-one, 8, (0.10, 0.26 mmol) in NMP (2 mL) is added amino tetrahydropyran (0.09 mL, 0.78 mmol). After stirring 1.5 hours at 90° C., the reaction mixture is diluted with methanol (to 5 mL) and is purified by reversed phase liquid chromatography (CH$_3$CN/water/1% TFA) to afford 44 mg (40%) of the desired product. $^1$H NMR (300 MHz, CDCl$_3$) δ 8.30 (d, J=5.1 Hz, 1H), 7.39-7.12 (m, 4H), 6.57 (d, J=5.1 Hz, 1H), 4.10-3.94 (m, 9H), 3.60-3.48 (m, 2H), 2.80-2.68 (m, 2H), 2.95-1.95 (m, 2H), 1.65-1.50 (m, 2H); ESI$^-$ MS: m/z (rel intensity) 426.0 (100, M$^+$–H).

The fourth aspect of Category II relates to R units which are substituted or unsubstituted aryloxy or alkylenearyloxy, non-limiting examples of which are described herein below in Table VIII.

TABLE VIII

| No. | R | R¹ |
|---|---|---|
| 169 | phenoxy | 2-methylphenyl |
| 170 | 2-chlorophenoxy | 2-methylphenyl |
| 171 | 3-chlorophenoxy | 2-methylphenyl |
| 172 | 2,6-dichlorophenoxy | 2-methylphenyl |
| 173 | 2-methylphenoxy | 2-methylphenyl |
| 174 | 2,6-dimethylphenoxy | 2-methylphenyl |
| 175 | 2-fluorophenoxy | 2-methylphenyl |
| 176 | 2,6-difluorophenoxy | 2-methylphenyl |
| 177 | phenoxy | 2-chlorophenyl |
| 178 | 2-chlorophenoxy | 2-chlorophenyl |
| 179 | 3-chlorophenoxy | 2-chlorophenyl |
| 180 | 2,6-dichlorophenoxy | 2-chlorophenyl |
| 181 | 2-methylphenoxy | 2-chlorophenyl |
| 182 | 2,6-dimethylphenoxy | 2-chlorophenyl |
| 183 | 2-fluorophenoxy | 2-chlorophenyl |
| 184 | 2,6-difluorophenoxy | 2-chlorophenyl |
| 185 | phenoxy | 4-fluorophenyl |
| 186 | 2-chlorophenoxy | 4-fluorophenyl |
| 187 | 3-chlorophenoxy | 4-fluorophenyl |
| 188 | 2,6-dichlorophenoxy | 4-fluorophenyl |
| 189 | 2-methylphenoxy | 4-fluorophenyl |
| 190 | 2,6-dimethylphenoxy | 4-fluorophenyl |
| 191 | 2-fluorophenoxy | 4-fluorophenyl |
| 192 | 2,6-difluorophenoxy | 4-fluorophenyl |

The following is a non-limiting example of the preparation of a compound which comprises the fourth aspect of Category II, said preparation utilizing intermediate 8 from Scheme II described herein above.

Preparation of 2-(2-chlorobenzyl)-3-(2-phenoxy-pyrimidin-4-yl)-6,7-dihydro-5H-pyrazolo[1,2-a]pyrazol-1-one: To a solution of phenol (0.18 g, 1.00 mmol) in THF (4 mL) is added sodium hydride (0.10 g of a 60% dispersion in mineral oil, 1.60 mmol). After stirring 5 min at room temperature a solution of 2-(2-chloro-benzyl)-3-(2-methanesulfonyl-pyrimidin-4-yl)-6,7-dihydro-5H-pyrazolo[1,2-a]pyrazol-1-one, 8, (0.21 g, 0.50 mmol) in THF (5 mL) is added to the reaction mixture. After stirring 1.5 h at room temperature, the mixture is diluted with aqueous saturated NaHCO$_3$. The aqueous phase is extracted three times with CHCl$_3$ and the combined organic phases are washed with aqueous saturated NaHCO$_3$, dried (MgSO$_4$), filtered and concentrated in vacuo. The crude residue is purified over silica (5% MeOH/CHCl$_3$) to afford 100 mg of the desired product as a yellow solid: $^1$H NMR (300 MHz, CDCl$_3$) δ 8.63 (d, J=5.4 Hz, 1H), 7.47 (t, J=7.8 Hz, 2H), 7.40 (d, J=5.4 Hz, 1H), 7.29-7.10 (m, 7H), 4.16 (t, J=6.9 Hz, 2H), 4.07 (s, 2H), 3.91 (t, J=6.9 Hz, 2H), 2.61 (dddd, J=6.9, 6.9, 6.9, 6.9 Hz, 2H); ESI$^+$ MS: m/z (rel intensity) 418.9 (100, M$^+$+H).

The compounds which comprise Category III of the present invention are 6,7-dihydro-5H-pyrazolo[1,2α]pyrazol-1-ones having the formula:

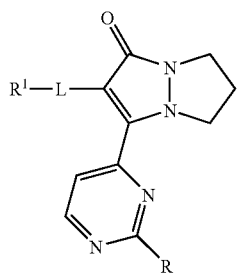

the first aspect of which relates to R units which are described herein above, R$^1$ unit which are substituted or unsubstituted aryl, and L units are —[C(R$^{12}$)$_2$]$_n$NR$^{12}$[C(R$^{12}$)$_2$]$_n$—, non-limiting examples of which are described herein below in Table IX.

TABLE IX

| No. | L | R | R$^1$ |
|---|---|---|---|
| 193 | —CH$_2$NHC(O)— | phenoxy | 2-methylphenyl |
| 194 | —CH$_2$NHC(O)— | 2-chlorophenoxy | 2-methylphenyl |
| 195 | —CH$_2$NHC(O)— | 3-chlorophenoxy | 2-methylphenyl |
| 196 | —CH$_2$NHC(O)— | 2,6-dichlorophenoxy | 2-methylphenyl |
| 197 | —CH$_2$NHC(O)— | 2-methylphenoxy | 2-methylphenyl |
| 198 | —CH$_2$NHC(O)— | 2,6-dimethylphenoxy | 2-methylphenyl |
| 199 | —CH$_2$NHC(O)— | 2-fluorophenoxy | 2-methylphenyl |
| 200 | —CH$_2$NHC(O)— | 2,6-difluorophenoxy | 2-methylphenyl |
| 201 | —CH$_2$NHC(O)— | phenoxy | 2-chlorophenyl |
| 202 | —CH$_2$NHC(O)— | 2-chlorophenoxy | 2-chlorophenyl |
| 203 | —CH$_2$NHC(O)— | 3-chlorophenoxy | 2-chlorophenyl |
| 204 | —CH$_2$NHC(O)— | 2,6-dichlorophenoxy | 2-chlorophenyl |
| 205 | —CH$_2$NHC(O)— | 2-methylphenoxy | 2-chlorophenyl |
| 206 | —CH$_2$NHC(O)— | 2,6-dimethylphenoxy | 2-chlorophenyl |
| 207 | —CH$_2$NHC(O)— | 2-fluorophenoxy | 2-chlorophenyl |
| 208 | —CH$_2$NHC(O)— | 2,6-difluorophenoxy | 2-chlorophenyl |
| 209 | —CH$_2$NHC(O)— | phenoxy | 4-fluorophenyl |
| 210 | —CH$_2$NHC(O)— | 2-chlorophenoxy | 4-fluorophenyl |
| 211 | —CH$_2$NHC(O)— | 3-chlorophenoxy | 4-fluorophenyl |
| 212 | —CH$_2$NHC(O)— | 2,6-dichlorophenoxy | 4-fluorophenyl |
| 213 | —CH$_2$NHC(O)— | 2-methylphenoxy | 4-fluorophenyl |
| 214 | —CH$_2$NHC(O)— | 2,6-dimethylphenoxy | 4-fluorophenyl |
| 215 | —CH$_2$NHC(O)— | 2-fluorophenoxy | 4-fluorophenyl |
| 216 | —CH$_2$NHC(O)— | 2,6-difluorophenoxy | 4-fluorophenyl |

The compounds which comprise the first aspect of Category III of the present invention can be prepared by the procedure outlined herein below in Scheme III.

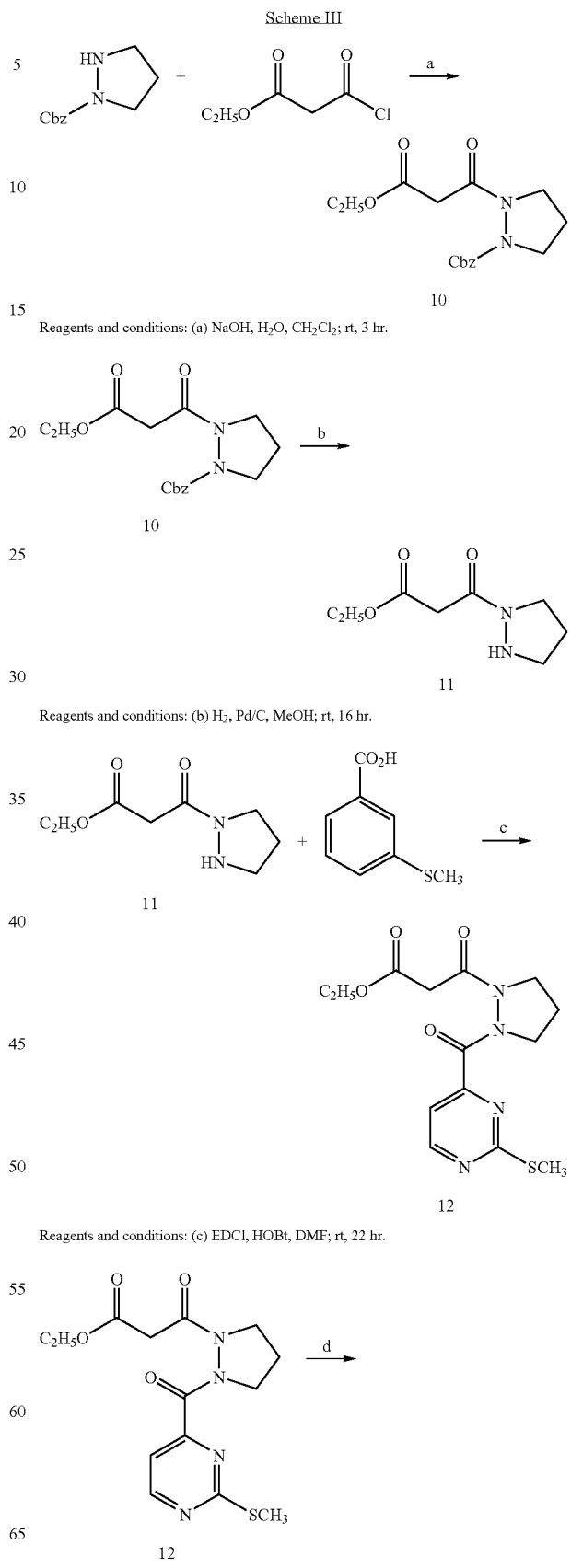

Scheme III

Reagents and conditions: (a) NaOH, H$_2$O, CH$_2$Cl$_2$; rt, 3 hr.

Reagents and conditions: (b) H$_2$, Pd/C, MeOH; rt, 16 hr.

Reagents and conditions: (c) EDCl, HOBt, DMF; rt, 22 hr.

-continued

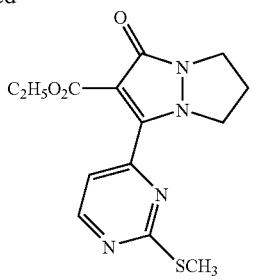

13

Reagents and conditions: (d) DBU, DMF; rt, 2 hr.

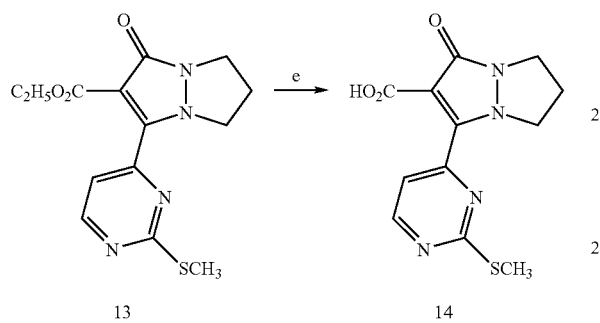

13 → 14

Reagents and conditions: (e) NaOH, THF/H₂O; rt, 1.5 hr.

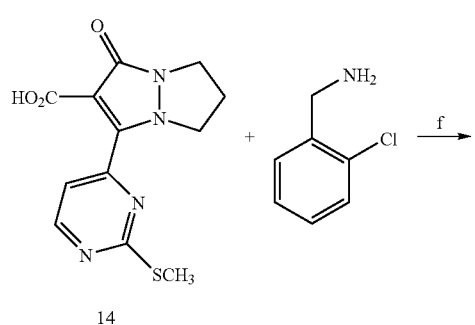

14

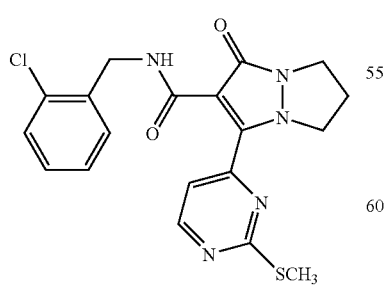

15

Reagents and conditions: (f) EDCl, HOBt, DMF; rt, 6 days.

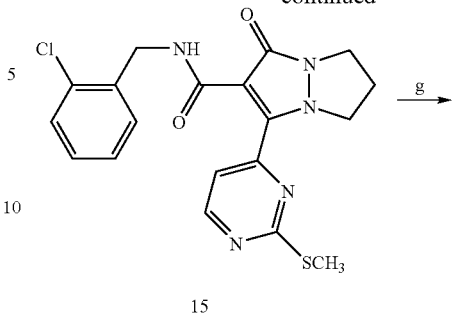

15

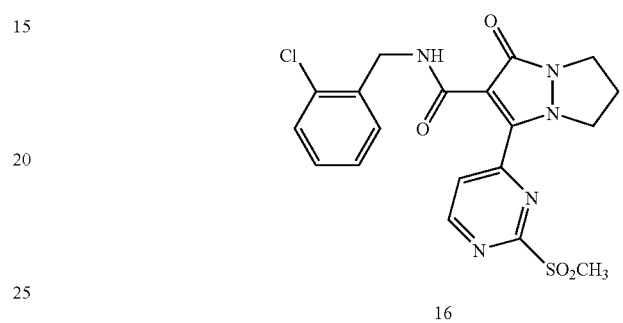

16

Reagents and conditions: (g) Oxone, THF/MeOH; rt, 1.5 hr.

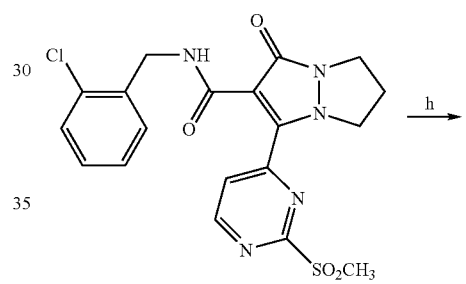

16

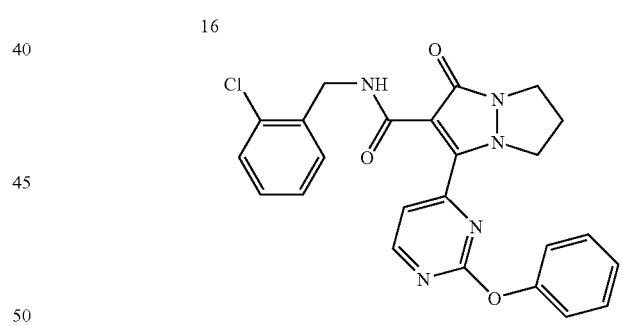

17

Reagents and conditions: (h) NaH, phenol, THF; rt, 1.5 hr.

EXAMPLE 3

1-Oxo-3-(2-phenoxy-pyrimidin-4-yl)-6,7-dihydro-1H,5H-pyrazolo[1,2-a]pyrazole-2-carboxylic acid 2-chloro-benzylamide (17)

Preparation of 2-(2-Ethoxycarbonyl-acetyl)-pyrazolidine-1-carboxylic acid benzyl ester (10): To a solution of sodium hydroxide (93.0 mL of 1N solution, 93.0 mmol) is added CH₂Cl₂ (280 mL) followed by pyrazolidine-1-carboxylic acid benzyl ester (15.0 g, 61.8 mmol) and then ethyl-3-chloro-3-oxopropionate (11.1 mL, 86.5 mmol). After stirring the biphasic mixture vigorously for 3 hours at room temperature, the mixture is quenched by pouring into aqueous saturated NH$_4$Cl. The organic phase is dried (MgSO$_4$), filtered and concentrated in vacuo. The crude residue is purified over silica (10% EtOAc/hexanes) to afford 15.5 g (78% yield) of the desired product. $^1$H NMR (300 MHz, CDCl$_3$) δ 7.38 (s, 5H), 5.23 (dd, J=11.8, 8.4 Hz, 2H), 4.19-4.07 (m, 4H), 3.65 (d, J=15.9 Hz, 1H), 3.31 (d, J=15.9 Hz, 1H), 3.20-3.15 (m, 2H), 2.20-2.04 (m, 2H), 1.26 (t, J=7.2 Hz, 3H); ESI$^+$ MS: m/z (rel intensity) 321.0 (100, M$^+$+H).

Preparation of 3-oxo-3-pyrazolidin-1-yl propionic acid ethyl ester (11): A solution of 2-(2-ethoxycarbonyl-acetyl)-pyrazolidine-1-carboxylic acid benzyl ester, 10, (15.5 g, 48.0 mmol) in MeOH (300 mL) is flushed with Nitrogen gas. Palladium (1.5 g, 10 wt. % on activated carbon) is added to the reaction mixture. A hydrogen balloon is affixed to the flask and the solution is stirred at room temperature for 16 hour. The mixture is filtered through celite and washed thoroughly with MeOH. The filtrate is concentrated in vacuo to afford 8.8 g of the crude product which is used without further purification.

Preparation of 3-[2-(2-Methylsulfanyl-pyrimidine-4-carbonyl)-pyrazolidin-1-yl]-3-oxo-propionic acid ethyl ester (12): To a solution of the 3-oxo-3-pyrazolidin-1-yl propionic acid ethyl ester, 11, (8.8 g, 47.7 mmol) in DMF (165 mL) is added 2-methylsulfanyl-pyrimidine-4-carboxylic acid (8.5 g, 50.1 mmol), followed by 1-hydroxybenzotriazole (12.9 g, 95.5 mmol) and then 1-(3-dimethylaminopropyl)-3-ethylcarbodiimide hydrochloride (11.0 g, 57.3 mmol). The reaction mixture is stirred at room temperature for 22 hours then poured into aqueous saturated NaHCO$_3$. The aqueous phase is extracted three times with EtOAc and the combined organic phases are dried (MgSO$_4$), filtered and concentrated in vacuo to afford 10.5 g of the desired compound which is used without further purification.

Preparation of 3-(2-methylsulfanyl-pyrimidin-4-yl)-1-oxo-6,7-dihydro-1H,5H-pyrazolo[1,2-a]pyrazole-2-carboxylic acid ethyl ester (13): To a solution of 3-[2-(2-methylsulfanyl-pyrimidine-4-carbonyl)-pyrazolidin-1-yl]-3-oxo-propionic acid ethyl ester, 12, (9.6 g, 28.4 mmol) in DMF (280 mL) was added 1.8-diazabicyclo[5.4.0]-undec-7-ene (12.7 mL, 85.2 mmol). The reaction solution is stirred for 2 hours at room temperature then diluted with H$_2$O. The aqueous phase is extracted three times with CHCl$_3$. The combined organic phases are washed with aqueous saturated NH$_4$Cl (×3), dried (MgSO$_4$), filtered and concentrated in vacuo. The residue is purified over silica (5% MeOH/CHCl$_3$) to afford 3.1 g of the desired product. $^1$H NMR (300 MHz, CDCl$_3$) δ 8.67 (d, J=5.1 Hz, 1H), 7.61 (d, J=5.1 Hz, 1H), 4.33 (q, J=7.2 Hz, 2H), 4.31 (t, J=7.2 Hz, 2H), 4.09 (t, J=7.2 Hz, 2H), 2.74 (dddd, 7.2, 7.2, 7.2, 7.2 Hz, 2H), 2.61 (s, 3H), 1.35 (t, J=7.2 Hz, 3H); ESI$^+$ MS: m/z (rel intensity) 321.1 (100, M$^+$+H).

Preparation of 3-(2-methylsulfanyl-pyrimidin-4-yl)-1-oxo-6,7-dihydro-1H,5H-pyrazolo[1,2-α]pyrazole-2-carboxylic acid (14): To a solution of 3-(2-methylsulfanyl-pyrimidin-4-yl)-1-oxo-6,7-dihydro-1H,5H-pyrazolo[1,2-a]pyrazole-2-carboxylic acid ethyl ester, 13, (2.7 g, 8.4 mmol) in THF (85 mL) is added aqueous NaOH (42 mL of 1N solution, 42.0 mmol). The solution is stirred for 18 hours at room temperature then diluted with aqueous saturated NaHCO$_3$ and the aqueous phase is extracted twice with CHCl$_3$. The aqueous phase is then acidified to pH 1 with aqueous 1N HCl and extracted twice with CHCl$_3$. The combined organic layers are dried (MgSO$_4$), filtered and concentrated in vacuo to afford 2.3 g of the desired product which is used without further purification.

Preparation of 3-(2-methylsulfanyl-pyrimidin-4-yl)-1-oxo-6,7-dihydro-1H,5H-pyrazolo[1,2-α]pyrazole-2-carboxylic acid 2-chloro-benzylamide (15): To a solution of 3-(2-methylsulfanyl-pyrimidin-4-yl)-1-oxo-6,7-dihydro-1H,5H-pyrazolo[1,2-a]pyrazolo-2-carboxylic acid, 14, (0.23 g, 0.78 mmol) and 2-chlorobenzylamine (0.10 mL, 0.78 mmol) in DMF (3 mL) is added 1-hydroxybenzotriazole (0.21 g, 1.57 mmol) and then 1-(3-dimethylamino-propyl)-3-ethylcarbodiimide hydrochloride (0.18 g, 0.94 mmol). The reaction solution is stirred at room temperature for 6 days then poured into aqueous saturated NaHCO$_3$. The aqueous phase is extracted with three times with EtOAc and the combined organic phases are washed with aqueous saturated NH$_4$Cl, and H$_2$O, dried (MgSO$_4$), filtered and concentrated in vacuo to afford the desired product which is used without further purification: $^1$H NMR (300 MHz, CDCl$_3$) δ 9.49 (bd s, NH), 8.69 (d, J=5.1 Hz, 1H), 8.16 (d, J=5.1 Hz, 1H), 7.44-7.37 (m, 2H), 7.25-7.19 (m, 2H), 4.70 (d, J=5.4 Hz, 2H), 4.41 (t, J=7.2 Hz, 2H), 4.14 (t, J=7.2 Hz, 2H), 2.78 (dd, J=7.5, 7.5, 7.5, 7.5 Hz, 2H), 2.06 (s, 3H); ESI$^+$ MS: m/z (rel intensity) 415.9 (100, M$^+$+H).

Preparation of 3-(2-methanesulfonyl-pyrimidin-4-yl)-1-oxo-6,7-dihydro-1H,5H-pyrazolo[1,2-α]pyrazole-2-carboxylic acid 2-chloro-benzylamide (16): To a solution of 3-(2-methylsulfanyl-pyrimidin-4-yl)-1-oxo-6,7-dihydro-1H,5H-pyrazolo[1,2-a]pyrazole-2-carboxylic acid 2-chloro-benzylamide, 15, (0.20 g, 0.48 mmol) in THF/MeOH (8 mL of 1:1 mixture) was added dropwise a solution of Oxone® (potassium peroxymonosulfate) (in H$_2$O (8 mL). After stirring the reaction for 1.5 h at room temperature, the solution was poured into aqueous saturated NaHCO$_3$. The aqueous phase is extracted with CHCl$_3$ (×3). The combined organic phases are dried (MgSO4), filtered and concentrated in vacuo to afford the desired product which is used without further purification.

Preparation of 1-oxo-3-(2-phenoxy-pyrimidin-4-yl)-6,7-dihydro-1H,5H-pyrazolo[1,2-α]pyrazole-2-carboxylic acid 2-chloro-benzylamide (17): To a solution of phenol (0.09 g, 1.00 mmol) in THF (2 mL) is added sodium hydride (0.05 g of a 60% dispersion in mineral oil, 0.80 mmol). After stirring 5 min at room temperature a solution of 3-(2-methanesulfonyl-pyrimidin-4-yl)-1-oxo-6,7-dihydro-1H,5H-pyrazolo[1,2-a]pyrazole-2-carboxylic acid 2-chloro-benzylamide, 16, (0.18 g, 0.40 mmol) in THF (3 mL) is added to the reaction mixture. After stirring 1.5 h at room temperature, the mixture is diluted with aqueous saturated NaHCO$_3$. The aqueous phase is extracted with CHCl$_3$ (×3). The combined organic phases are washed with aqueous saturated NaHCO$_3$, dried (MgSO$_4$), filtered and concentrated in vacuo. The crude residue is purified over silica (5% MeOH/CHCl$_3$) to afford 110 mg of the desired product as a white solid: $^1$H NMR (300 MHz, CDCl$_3$) δ 9.59 (bd s, NH), 8.75 (d, J=5.1 Hz, 1H), 8.49 (d, J=7.2 Hz, 1H), 7.49-7.20 (m, 9H), 4.72 (d, J=5.4 Hz, 2H), 4.04 (t, J=7.2 Hz, 2H), 3.98 (t, J=7.2 Hz, 2H), 2.57 (dddd, J=6.9, 6.9, 6.9, 6.9 Hz, 2H); ESI$^+$ MS: m/z (rel intensity) 462.1 (100, M$^+$+H); HRMS m/z calcd for C$_{24}$H$_{20}$ClN$_5$O$_3$ (M+H+) 462.1333, found 462.1320.

The following are non-limiting examples of compounds according to the first aspect of Category III.

1-Oxo-3-(2-phenoxy-pyrimidin-4-yl)-6,7-dihydro-1H,5H-pyrazolo[1,2-a]pyrazole-2-carboxylic acid (2-chlorophenyl)-amide: $^1$H NMR (300 MHz, CDCl$_3$) δ 11.53 (s, NH), 8.79 (d, J=5.1 Hz, 1H), 8.50 (dd, J=8.1, 1.5 Hz, 1H), 8.41 (d, J=5.1 Hz, 1H), 7.48 (t, J=8.1 Hz, 2H), 7.41 (dd, J=8.1, 1.5 Hz, 1H), 7.34-7.21 (m, 5H), 7.03 (ddd, J=7.5, 7.5, 1.8 Hz, 1H), 6.94-6.85 (m, 1H), 4.09 (t, J=7.2 Hz, 2H), 4.01 (t, J=7.2 Hz, 2H), 2.62 (dddd, J=7.2, 7.2, 7.2, 7.2 Hz, 2H); ESI$^+$ MS: m/z (rel intensity) 447.9./(100, M$^+$+H); HRMS m/z calcd for C$_{24}$H$_{20}$ClN$_5$O$_3$ (M+H+) 462.1333, found 462.1320.

The compounds which comprise Category IV of the present invention are 6,7-dihydro-5H-pyrazolo[1,2α]pyrazol-1-ones having the formula:

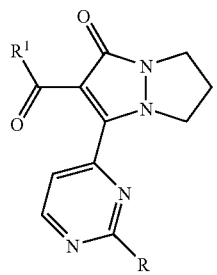

the first aspect of which relates to R units which are described herein above, $R^1$ unit which are substituted or unsubstituted aryl, and L units are —[C(R$^{12}$)$_2$]— wherein two $R^{12}$ units are taken together to form a carbonyl unit, non-limiting examples of which are described herein below in Table X.

TABLE X

| No. | R | $R^1$ |
|---|---|---|
| 217 | phenoxy | 2-methylphenyl |
| 218 | 2-chlorophenoxy | 2-methylphenyl |
| 219 | 3-chlorophenoxy | 2-methylphenyl |
| 220 | 2,6-dichlorophenoxy | 2-methylphenyl |
| 221 | 2-methylphenoxy | 2-methylphenyl |
| 222 | 2,6-dimethylphenoxy | 2-methylphenyl |
| 223 | 2-fluorophenoxy | 2-methylphenyl |
| 224 | 2,6-difluorophenoxy | 2-methylphenyl |
| 225 | phenoxy | 2-chlorophenyl |
| 226 | 2-chlorophenoxy | 2-chlorophenyl |
| 227 | 3-chlorophenoxy | 2-chlorophenyl |
| 228 | 2,6-dichlorophenoxy | 2-chlorophenyl |
| 229 | 2-methylphenoxy | 2-chlorophenyl |
| 230 | 2,6-dimethylphenoxy | 2-chlorophenyl |
| 231 | 2-fluorophenoxy | 2-chlorophenyl |
| 232 | 2,6-difluorophenoxy | 2-chlorophenyl |
| 233 | phenoxy | 4-fluorophenyl |
| 234 | 2-chlorophenoxy | 4-fluorophenyl |
| 235 | 3-chlorophenoxy | 4-fluorophenyl |
| 236 | 2,6-dichlorophenoxy | 4-fluorophenyl |
| 237 | 2-methylphenoxy | 4-fluorophenyl |
| 238 | 2,6-dimethylphenoxy | 4-fluorophenyl |
| 239 | 2-fluorophenoxy | 4-fluorophenyl |
| 240 | 2,6-difluorophenoxy | 4-fluorophenyl |

The compounds which comprise the first aspect of Category IV of the present invention can be prepared by the procedure outlined herein below in Scheme IV.

Scheme IV

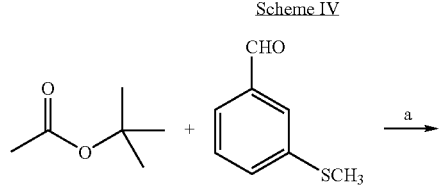

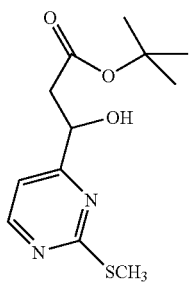

Reagents and conditions: (a) n-butyllithium, DIPA, THF; -78° C., 30 min.

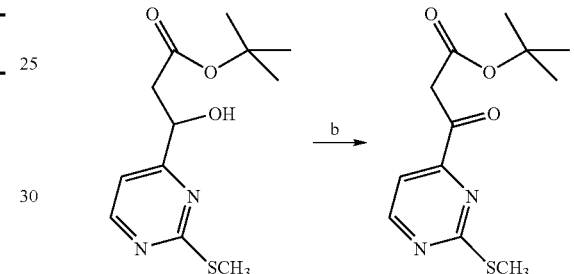

Reagents and conditions: (b) Dess-martin periodinane, H$_2$O; rt, 1 hr.

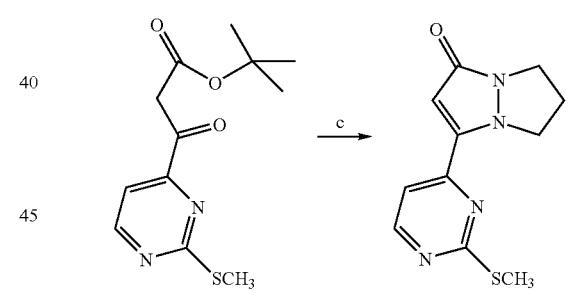

Reagents and conditions: (c) pyrazolidine, TEA; reflux, 4 hr.

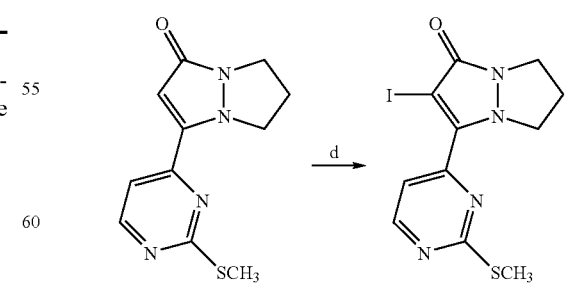

Reagents and conditions: (d) I$_2$, CCL$_4$/pyridine; 0° C., 30 min.

-continued

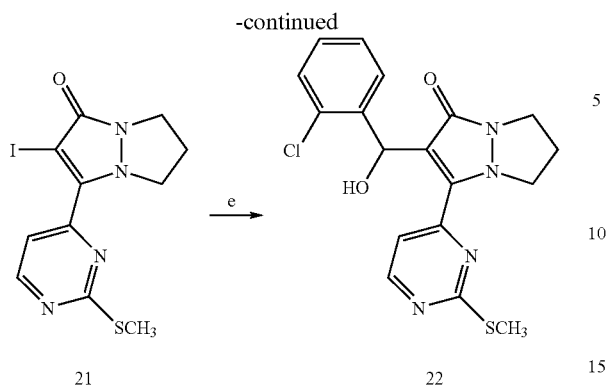

Reagents and conditions: (e) isopropylmagnesium chloride, 2-chlorobenzaldehyde, THF; -40° C. to 0° C., 1 hr.

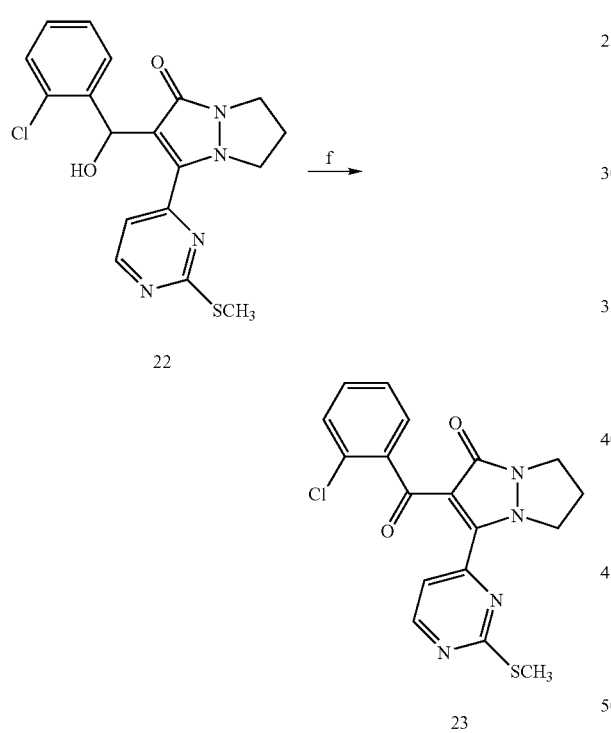

Reagents and conditions: (f) MnO₂, CH₂Cl₂; rt, 18 hr.

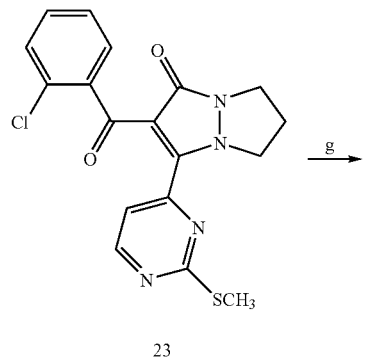

-continued

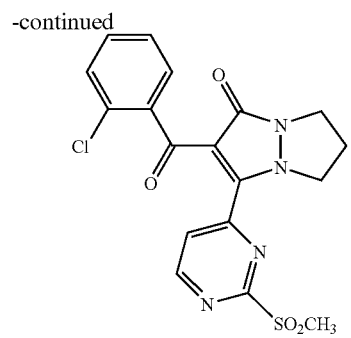

Reagents and conditions: (d) Oxone THF/MeOH; rt, 1.5 hr.

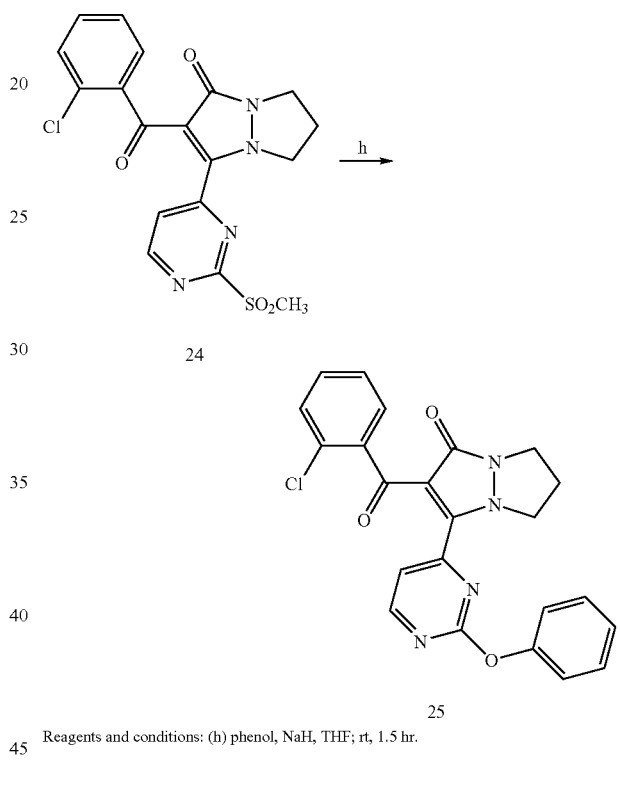

Reagents and conditions: (h) phenol, NaH, THF; rt, 1.5 hr.

EXAMPLE 4

2-(2-Chlorobenzoyl)-3-(2-phenoxy-pyrimidin-4-yl)-6,7-dihydro-5H-pyrazolo[1,2-a]pyrazol-1-one (25)

The following is a procedure for the preparation of 2-methylsulfanyl-pyrimidine-4-carbaldehyde adapted from the procedure of H. Bredereck et al., *Chem. Ber.,* 97, pp 3407-3417 (1964) included herein by reference.

To a 12 L 3-neck flask under inert atmosphere is charged N,N-dimethyl-formamide dimethyl acetyl (801 g) and pyruvic aldehyde dimethyl acetal (779 g). The mixture is heated to reflux for 18 hours during which time the temperature decreases from about 109° C. to about 80° C. The solution is cooled and methanol (4 L) is added to dissolve the crude residue. The solution is then cooled to 20° C. and thiourea (892 g, 11.7 mol) is added. After allowing the mixture to stir about 15 minutes, sodium methoxide (741 g, 13.7 mol) is added in 4 equal portions over 1 hour while maintaining the solution temperature in the range of 18-28° C. The mixture is stirred for 5 hours at room temperature, cooled to 20° C., then methyl iodide (2 kg) is added over 1.25 hours while maintaining the reaction temperature in the range of 17-29° C. Stirring is continued for 18 hours at room temperature. The methanol and unreacted methyl iodide is removed by heating the solution at 35° C. @ 40 torr to produce about 4.46 kg of a dark residue which is partitioned between 14 L of water and 5 L of ethyl acetate. The water fraction is extracted a second time with ethyl acetate, the organic layers combined and concentrated in vacuo too afford 685 g of an oil which is purified over silica to 522 g of 4-dimethoxymethyl-2-methylsulfanyl-pyrimidine.

The dimethyl acetal obtained above is then hydrolyzed to the free aldehyde by heating to 60° C. for 3 hours in 1M HCl. Workup for neutral using ethyl acetate to extract the product affords 347 g crude product which is purified over silica to afford 401 g of 2-methylsulfanyl-pyrimidine-4-carbaldehyde.

Preparation of 3-hydroxy-3-(2-methylsulfanyl-pyrimidin-4-yl)-propionic acid tert-butyl ester (18): To a cold (0° C.) solution of diisopropylamine (5.7 mL, 40.5 mmol) in THF (130 mL) is added dropwise n-butyllithium (16.2 mL of a 2.5 M solution in hexanes, 40.5 mmol). The mixture is stirred for 45 min at 0° C., then the solution is cooled to −78° C. tert-Butyl acetate (5.5 mL, 40.5 mmol) is added dropwise to the reaction mixture. After stirring 40 min at −78° C., a solution of 2-methylsulfanyl-pyrimidine-4-carbaldehyde (5.0 g, 32.4 mmol) is added dropwise. After 30 min at −78° C., the solution is poured into aqueous saturated $NH_4Cl$. The aqueous phase is extracted with EtOAc. The organic phase is dried ($MgSO_4$), filtered and concentrated in vacuo. The crude residue is purified over silica (5% EtOAc/hexanes, followed by 20% EtOAc/hexanes) to afford 7.2 g (82% yield) of the desired product. $^1H$ NMR (300 MHz, $CDCl_3$) δ 8.52 (d, J=5.1 Hz, 1H), 7.22 (d, J=5.1 Hz, 1H), 5.00 (dd, J=8.4, 3.6 Hz, 1H), 2.93 (dd, J=16.5, 3.6 Hz, 1H), 2.70 (dd, J=16.5, 7.8 Hz, 1H), 2.58 (s, 3H), 1.46 (s, 9H); $ESI^+$ MS: m/z (rel intensity) 271.1 (85, $M^++H$).

Preparation of 3-(2-methylsulfanyl-pyrimidin-4-yl)-3-oxo-propionic acid tert-butyl ester (19): To a solution of 3-hydroxy-3-(2-methylsulfanyl-pyrimidin-4-yl)-propionic acid tert-butyl ester, 18, (5.6 g, 20.9 mmol) in $CH_2Cl_2$ is added Dess-Martin periodinane (10.7 g, 25.1 mmol) followed by $H_2O$ (0.5 mL, 25.1 mmol). After stirring 1 h at room temperature, the solution is poured into aqueous saturated $Na_2S_2O_4$. The aqueous phase is extracted with $CH_2Cl_2$, then EtOAc. The combined organic phases are dried ($MgSO_4$), filtered and concentrated in vacuo. The crude residue is purified over silica (10% EtOAc/hexanes) to afford 5.6 g (95% yield) of the desired product. $^1H$ NMR (300 MHz, $CDCl_3$) (observed 3:1 mixture of enol:keto tautomers) enol tautomer: δ 12.34 (s, OH), 8.67 (d, J=5.1 Hz, 1H), 7.48 (d, J=5.1 Hz, 1H), 6.35 (s, 1H), 2.62 (s, 3H), 1.57 (s, 9H); $ESI^+$ MS: m/z (rel intensity) 269.1 (30, $M^++H$).

Preparation of 3-(2-methylsulfanyl-pyrimidin-4-yl)-6,7-dihydro-5H-pyrazolo[1,2-a]pyrazol-1-one (20): To a solution of 3-(2-methylsulfanyl-pyrimidin-4-yl)-3-oxo-propionic acid tert-butyl ester, 19, (6.8 g, 25.4 mmol), pyrazolidine-bishydrochloride (5.5 g, 38.1 mmol) and 4-angstrom molecular sieves (8.5 g) in toluene is added triethylamine (10.6 mL, 76.1 mmol). The reaction mixture is stirred for 4 hours at reflux. The solution is filtered through celite and washed with ether. The resulting yellow solid is purified over silica (10% MeOH/chloroform) to afford 5 g of the desired product as a yellow solid: $^1H$ NMR (300 MHz, $CDCl_3$) δ 8.72 (d, J=5.1 Hz, 1H), 7.62 (d, J=5.1 Hz, 1H), 6.08 (s, 1H), 4.26 (t, J=7.5 Hz, 2H), 3.80 (t, J=7.8 Hz, 2H), 2.62 (dddd, J=7.5, 7.5, 7.5, 7.5 Hz, 2H), 2.60 (s, 3H); $ESI^+$ MS: m/z (rel intensity) 249.1 (70, $M^++H$).

Preparation of 2-iodo-3-(2-methylsulfanyl-pyrimidin-4-yl)-6,7-dihydro-5H-pyrazolo[1,2-a]pyrazol-1-one (21): To a cold (0° C.) solution of 3-(2-methylsulfanyl-pyrimidin-4-yl)-6,7-dihydro-5H-pyrazolo[1,2-a]pyrazol-1-one, 20, (4.7 g, 19.1 mmol), in carbon tetrachloride/pyridine (140 mL of 1:1 mixture) is added dropwise a solution of iodine in carbon tetrachloride/pyridine (80 mL of 1:1 mixture). After stirring at 0° C. for 30 min, the ice-bath is removed at the mixture was stirred at room temperature. After stirring at room temperature for 1 hour, the reaction mixture was poured into aqueous saturated $Na_2S_2O_3$. The aqueous phase is extracted with EtOAc (×3). The combined organic phases are dried ($MgSO_4$), filtered and concentrated in vacuo. The resulting yellow solid is purified by silica gel chromatography (5% MeOH/chloroform) to afford 4.2 g of the desired product. $^1H$ NMR (300 MHz, $CDCl_3$) δ 8.72 (d, J=5.1 Hz, 1H), 7.97 (d, J=5.1 Hz, 1H), 4.31 (t, J=6.9 Hz, 2H), 4.10 (t, J=6.9 Hz, 2H), 2.74 (dddd, J=6.9, 6.9, 6.9, 6.9 Hz, 2H), 2.62 (s, 3H); $ESI^+$ MS: m/z (rel intensity) 375.0 (100, $M^++H$).

Preparation of 2-[(2-chlorophenyl)-hydroxy-methyl]-3-(2-methylsulfanyl-pyrimidin-4-yl)-6,7-dihydro-5H-pyrazolo[1,2-a]pyrazol-1-one (22): To a cold (−40° C.) suspension of 2-iodo-3-(2-methylsulfanyl-pyrimidin-4-yl)-6,7-dihydro-5H-pyrazolo[1,2-a]pyrazol-1-one, 21, (0.40 g, 1.07 mmol) in THF (3 mL) is added dropwise isopropyl-magnesium chloride (0.59 mL of a 2M solution in THF, 1.18 mmol). After stirring for 30 min at −40° C., a solution of 2-chlorobenzaldehyde (0.16 mL, 1.40 mmol) is added dropwise. The reaction mixture is allowed to warm to 0° C. over 1 h period. The mixture is quenched by pouring into aqueous saturated $NH_4Cl$. The aqueous phase is extracted three times with EtOAc and the combined organic phases are dried ($MgSO_4$), filtered and concentrated in vacuo. The crude residue is purified over silica (10% MeOH/chloroform) to afford 240 mg (58% yield) of desired product. $^1H$ NMR (300 MHz, $CDCl_3$) δ 8.56 (d, J=5.1 Hz, 1H), 7.78 (dd, J=7.2, 1.8 Hz, 1H), 7.34-7.18 (m, 2H), 7.01 (d, J=5.1 Hz, 1H), 6.21 (s, 1H), 4.20-4.01 (m, 5H), 2.80-2.70 (m, 2H), 2.58 (s, 3H); $ESI^+$ MS: m/z (rel intensity) 371.1 (100, $M^++H$).

Preparation of 2-(2-chlorobenzoyl)-3-(2-methylsulfanyl-pyrimidin-4-yl)-6,7-dihydro-5H-pyrazolo[1,2-a]pyrazol-1-one (23): To a solution of 2-[(2-chloro-phenyl)-hydroxy-methyl]-3-(2-methylsulfanyl-pyrimidin-4-yl)-6,7-dihydro-5H-pyrazolo[1,2-a]pyrazol-1-one, 22, (0.22 g, 0.56 mmol) in $CH_2Cl_2$ (3 mL) is added manganese (IV) oxide (0.30 g, 3.40 mmol). After stirring for 18 hours at room temperature, the mixture is filtered through celite and washed with $CH_2Cl_2$. The filtrate is concentrated in vacuo. The crude residue is purified over silica (5% MeOH/chloroform) to afford 165 mg (69% yield) of the desired product. $^1H$ NMR (300 MHz, $CDCl_3$) δ 8.69 (d, J=5.1 Hz, 1H), 7.78 (dd, J=7.2, 1.8 Hz, 1H), 7.81 (d, J=5.1 Hz, 1H), 7.46-7.33 (m, 4H), 4.44 (t, J=7.2 Hz, 2H), 4.03 (t, J=7.2 Hz, 2H), 2.76 (dddd, J=7.2, 7.2, 7.2, 7.2 Hz, 2H), 2.63 (s, 3H); $ESI^+$ MS: m/z (rel intensity) 387.1 (100, $M^++H$).

Preparation of 2-(2-chlorobenzoyl)-3-(2-methanesulfonyl-pyrimidin-4-yl)-6,7-dihydro-5H-pyrazolo[1,2-a]pyrazol-1-one (24): To a solution of 2-(2-chloro-benzoyl)-3-(2-methylsulfanyl-pyrimidin-4-yl)-6,7-dihydro-5H-pyrazolo[1,2-a]pyrazol-1-one, 23, (0.15 g, 0.39 mmol)) in THF/MeOH (3 mL of 1:1 mixture) is added dropwise a solution of Oxone® (potassium peroxymonosulfate) (0.72 g, 1.16 mmol) in $H_2O$ (3 mL). After stirring the reaction for 1.5 hour at room temperature, the solution is poured into aqueous saturated $NaHCO_3$. The aqueous phase is extracted three times with $CHCl_3$ and the combined organic phases are dried (MgSO4), filtered and concentrated in vacuo. The crude product is used without further purification.

Preparation of 2-(2-chlorobenzoyl)-3-(2-phenoxy-pyrimidin-4-yl)-6,7-dihydro-5H-pyrazolo[1,2-a]pyrazol-1-one (25): To a solution of phenol (0.04 g, 0.43 mmol) in THF (1 mL) is added sodium hydride (0.02 g of a 60% dispersion in mineral oil, 0.32 mmol). After stirring 5 min at room temperature a solution of 2-(2-chloro-benzoyl)-3-(2-methanesulfonyl-pyrimidin-4-yl)-6,7-dihydro-5H-pyrazolo[1,2-a]pyrazol-1-one, 24, (0.09 g, 0.21 mmol) in THF (2 mL) is added to the reaction mixture. After stirring 1.5 hours at room temperature, the mixture is diluted with aqueous saturated $NaHCO_3$. The aqueous phase is extracted three times with $CHCl_3$ and the combined organic phases are washed with aqueous saturated $NaHCO_3$, dried ($MgSO_4$), filtered and concentrated in vacuo. The crude residue is purified over silica (10% $MeOH/CHCl_3$) to afford 30 mg of the desired product. $^1H$ NMR (300 MHz, $CDCl_3$) δ 8.77 (d, J=5.1 Hz, 1H), 8.04 (d, J=5.1 Hz, 1H), 7.49 (t, J=7.8 Hz, 1H), 7.41-7.20 (m, 9H), 4.00 (t, J=7.2 Hz, 2H), 3.95 (t, J=7.2 Hz, 2H), 2.54 (dddd, J=7.5, 7.5, 7.5, 7.5 Hz, 2H); ESI$^-$ MS: m/z (rel intensity) 431.1 (100, $M^+$–H).

The following is a non-limiting example of compounds which comprise the second aspect of Category III.

2-(2-Chloro-benzyl)-3-[2-(2-methoxy-1-methyl-ethylamino)-pyrimidin-4-yl]-6,7-dihydro-5H-pyrazolo[1,2-a]pyrazol-1-one: $^1H$ NMR (300 MHz, $CDCl_3$) δ 8.14 (d, J=5.1 Hz, 1H), 7.38 (d, J=5.4 Hz, 1H), 7.18-7.10 (m, 3H), 6.61 (d, J=5.4 Hz, 1H), 4.40-4.23 (m, 5H), 4.07 (s, 2H), 3.45 (d, J=5.4 Hz, 2H), 3.38 (s, 3H), 2.82 (dddd, J=6.9, 6.9, 6.9, 6.9 Hz, 2H); ESI$^-$ MS: m/z (rel intensity) 413.9 (100, $M^+$+H).

Compounds listed and described herein above have been found in many instances to exhibit activities ($IC_{50}$ in the cell based assay described herein below or ones which are referenced herein) at a level below 1 micromolar (μM).

Each of the disease states or conditions which the formulator desires to treat may require differing levels or amounts of the compounds described herein to obtain a therapeutic level. The formulator can determine this amount by any of the known testing procedures known to the artisan.

Diseases Affected by Cytokine Activity

The following diseases are affected by the presence of undesirable levels of extracellular cytokines.
A) The analogs of the present invention are directed to the interruption of the extracellular release of Interleukin-1 (IL-1) which has been implicated as the molecule responsible for a large number of disease states, inter alia, rheumatoid arthritis,[1,2,3] osteoarthritis,[4,5,6,7,8,9] as well as other disease states which relate to connective tissue degradation (periodontal disease, muscle degeneration).[10]
B) The analogs of the present invention are also directed to the interruption of the extracellular release of Cycloxygenase-2 (COX-2), which has been shown to be increased by cytokines.[11] Disease states and conditions which are assertedly affected by COX-2 include fever, malaise, myalgia, and headache.[12]
C) The analogs of the present invention are further directed to the interruption of the extracellular release of Tumor Necrosis Factor-α (TNF-α). This pro-inflammatory cytokine is suggested as an important mediator in many disease states or syndromes, inter alia, rheumatoid arthritis, osteoarthritis, acute and chronic inflammatory diseases, which are induced by endotoxin, or irritable bowel disease (IBD), Crohn's, and ulcerative colitis, septic shock, cardiopulmonary dysfunction, acute respiratory disease, and cachexia.
D) The analogs of the present invention which are effective antagonists are capable of modulation, controlling, or otherwise abating the unwanted release of unwanted cytokines or excess cytokines or can be used to treat other disease states relating to cytokine activity. Non-limiting examples of diseases or disease states linked to cytokine activity include congestive heart failure; hypertension;[13] chronic obstructive pulmonary disease (COPD) and septic shock syndrome;[14] tuberculosis, adult respiratory distress syndrome, asthma;[15] atherosclerosis;[16] muscle degeneration and periodontal disease;[17] cachexia, Reiter's syndrome, gout, acute synovitis, eating disorders, inter alia, anorexia and bulimia nervosa;[18] fever, malaise, myalgia and headaches.[19]

In addition, other disease states have been linked to cytokine activity. Non-limiting examples of diseases, disease states, syndromes (both chronic and acute) which are related to unwanted or over release of inflammatory cytokines include diabetes[20] and HIV/AIDS.[21]

The following are non-limiting examples of the connection between over activity, over expression, and unwanted extracellular release of cytokines and diseases and disease states.

Congestive Heart Failure

Tumor Necrosis Factor-alpha (TNF-α), as well as other pro-inflammatory cytokines, inter alia, Interleukin-1β(IL-1β) and IL-6, have been found in patients with advanced heart failure due to ischemic or idiopathic cardiomyopathies.[22,23,24,25] For example, Aukrust et al.[26] have found that patients with congestive heat failure have elevated plasma levels of inflammatory cytokines, inter alia, TNF-α, IL-1β.

It has been found by Behr et al.[27] that volume-overload congestive heart failure in rats is associated with alterations in the expression and receptor binding of the cytokine, monocyte chemoattractant protein-1 (MCP-1). It is therefore well established that inhibition of cytokines, for example, by 6,7-dihydro-5H-pyrazolo[1,2α]pyrazol-1-ones according to the present invention which inhibit the extracellular release of inflammatory cytokines, are effective as a method for controlling, mediating, or otherwise modulating congestive heart failure or other cardiac diseases associated with the unwanted release of extracellular cytokines.

Crohn's Disease

Compounds which affect the activity of Tumor Necrosis Factor-alpha (TNF-α), for example, selective analogs according to the present invention, have been shown to mediate Crohn's disease.

For example, Stack et al.[28] exposed patients in a double blind test to a genetically engineered human antibody to TNF-α, CDP571. A single 5 mg/kg infusion of this TNF-α activity modulating antibody reduced disease activity in Crohn's disease at 2 weeks. Data such as these suggest that neutralization of TNF-α, for example, by an antibody or other factor such as a compound which inhibits cytokine activity, is an effective strategy in the management of Crohn's disease. The compounds of the present invention capable of inhibiting TNF-α are suitable for use in a method of treating Crohn's disease.

Each of the disease states or conditions which the formulator desires to treat may require differing levels or amounts of the compounds described herein to obtain a therapeutic level. The formulator can determine this amount by any of the known testing procedures known to the artisan.

The following relate to the connection between cytokine activity and diseases or disease states and are included herein by reference.

1. Dinarello, C. A. et al., *Rev Infect Disease,* 6:51, (1984).
2. Maini, R. E., *The Lancet,* 354: 1932, (1999).
3. Weinblatt, M. E., *New England Journal of Medicine,* 340, 253, (1999).
4. Pelletier and Pelletier, *J Rheum,* 16:19, (1989).
5. Pelletier et al., *Am J Path,* 142:95, (1993).
6. Farahat et al., *Ann Rheum Dis,* 52:870, (1993).
7. Tiku et al, *Cell Immunol,* 140:1, (1992).

8. Webb et al., *O and C*, 5:427, (1997).
9. Westacott et al., *O and C*, 8:213, (2000).
10. Howells, *Oral Diseases*, 1:266, (1995).
11. M. K. O'Banion et al., *Proc. Natl. Acad. Sci. U.S.A.*, 89, 4888 (1998).
12. Beisael, *American Journal of Clinical Nutrition*, 62:813, (1995).
13. Singh, et al., *Journal of Hypertension*, 9:867 (1996);
14. Dinarello, C. A., *Nutrition* 11:492 (1995);
15. Renzetti, et al. *Inflammation Res.* 46:S143;
16. Elhage, et al., *Circulation* 97:242 (1998);
17. Howells, *Oral Dis.* 1:266 (1995); .
18. Holden, et al., *Medical Hypothesis* 47:423 (1996);
19. Beisel, *American Journal of Clinical Nutrition*, 62:813 (1995).
20. McDaniel et al., *Proc Soc, Exp, Biol Med*, 211:24, (1996).
21. Kreuzer et al., *Clinical Experiments Immunology*, 45:559, (1997).
22. Levine B, Kalman J, Mayer L, et al. Elevated circulating levels of tumor necrosis factor in severe chronic heart failure. *New England Journal of Medicine*, 323, 236-241 (1990).
23. Dutka D P, Elborn J S, Delamere F, et al., Tumor necrosis factor alpha in severe congestive cardiac failure. *British Heart Journal*, 70 141-143 (1993).
24. Torre-Amione G, Kapadia S, Lee J, et al. Tumor necrosis factor-α and tumor necrosis factor receptors in the failing human heart. *Circulation*, 93, 704-711 (1996).
25 Packer M. Is tumor necrosis factor an important neurohormonal mechanism in chronic heart failure? *Circulation*, 92, 1379-1382 (1995).
26. Pål Aukrust et al., Cytokine Network in Congestive Heart Failure Secondary to Ischemic or Idiopathic Dilated Cardiomyopathy, *American Journal of Cardiology*, 83, 376-382 (1999).
27. Behr T M et al., Monocyte Chemoattractant Protei-1 is Upregulated in Rats with Volume-Overload Congestive Heart Failure, *Circulation*, 102, 1315-1322 (2000).
28. Stack, W A; Mann, S D; Roy, A J; et al., *The Lancet*; Feb. 22, 1977; 349, 9051.

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Pro-drug Forms

Related to this aspect are the various precursor or "pro-drug" forms of the analogs of the present invention. It may be desirable to formulate the compounds of the present invention as a chemical species which itself is not an antagonist against melanin concentrating hormone as described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. The term "pro-drug" relates to these species which are converted in vivo to the active pharmaceutical.

The pro-drugs of the present invention can have any form suitable to the formulator, for example, esters are common pro-drug forms. In the present case, however, the pro-drug may necessarily exist in a form wherein a covalent bond is cleaved by the action of an enzyme present at the target situs. For example, a C-C covalent bond may be selectively cleaved by one or more enzymes at said target situs and, therefore, a pro-drug in a form other than an easily hydrolysable precursor, inter alia, esters, amides, and the like, may be utilized.

For the purposes of the present invention the term "therapeutically suitable pro-drug" is defined herein as "a melanin concentrating hormone antagonist modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome."

A detailed description of pro-drug derivatives can be found in the following included herein by reference:
a) *Design of Produrgs*, edited by H. Bundgaard, (Elsevier, 1985);
b) *Methods in Enzymology*, 42, 309-396, edited by K. Widder et al. (Academic Press, 1985);
c) *A Textbook of Drug Design and Development*, edited by Krogsgaard-Larsen and H. Bundgaard, Chapter 5, "Design and Application of Prodrugs." By H. Bundgaard, 113-191 (1991);
d) *Advance Drug Delivery Reviews*, H. Bundgaard, 8, 1-38 (1992);
e) *Chem Pharm Bull*, N. Kakeya et al., 32, 692 (1984).

Formulations

The present invention also relates to compositions or formulations which comprise the inflammatory cytokine release-inhibiting compounds according to the present invention. In general, the compositions of the present invention comprise:
a) an effective amount of one or more 6,7-dihydro-5H-pyrazolo[1,2α]pyrazol-1-ones and derivatives thereof according to the present invention which are effective for inhibiting release of inflammatory cytokines; and
b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present invention also relates to compositions or formulations which comprise a precursor or "pro-drug" form of the inflammatory cytokine release-inhibiting compounds according to the present invention. For the purposes of the present invention, as it relates to the subject of chemical entities which are converted in vivo to 6,7-dihydro-5H-pyrazolo[1,2α]-pyrazol-1-ones, the terms "pro-drug," "derivative," and "precursor" are considered to be interchangeable and represent the same concept. In general, these precursor-comprising compositions of the present invention comprise:
a) an effective amount of one or more derivatives or prodrug of 6,7-dihydro-5H-pyrazolo[1,2α]pyrazol-1-ones according to the present invention which act to release in vivo the corresponding analog which is effective for inhibiting release of inflammatory cytokines; and b) one or more pharmaceutically acceptable excipients.

The present invention also relates to compositions or formulations which comprise the inflammatory cytokine release-inhibiting compounds according to the present invention effective in providing analgesia. In general, the compositions of the present invention comprise:

a) an effective amount of one or more 6,7-dihydro-5H-pyrazolo[1,2α]pyrazol-1-ones and derivatives or pro-drugs thereof according to the present invention which are effective for inhibiting release of inflammatory cytokines;

b) an effective amount of one or more compounds having pain relief properties; and c) one or more pharmaceutically acceptable excipients.

The following are non-limiting examples of compounds having pain relief properties or compounds which are effective in providing relief from pain and which can be suitably combined with the compounds of the present invention:

Acetaminophen, aspirin, difunisal, dipyrone, ibuprofen, naproxen, fenoprofen, fenbufen, ketoprofen, flurbiprofen, indomethacin, ketorolac, diclofenac, floctafenine, piroxicam, celecoxib, and rofecoxib.

The following are non-limiting of adjunct ingredients which may be combined with the compounds of the present invention: Caffeine, compatible amphetamines, compatible antihistamines, compatible antidepressants.

In addition, opioid narcotic analgesics may be combined to form pharmaceutical compositions, for example, oxycodone (Percadan, Percacet, Oxycontin, Tylox), pethidine/meperidine (Demerol), methadone (Physeptone, Dolphine), levorphanol (Dromoran, Levodromoran), hydromorphone (Dilaudid), and buprenorpnine (Temgesic).

The term "effective amount" is defined herein as an amount which achieves the desired pharmaceutical result but which is also within the realm of safe medical practices." For example, it is long been known that the use of some pharmaceutically active compounds, inter alia, opiates, can lead to physical or psychological dependency. The amount which comprises the compositions of the present invention can be of varying amounts depending upon the active ingredient, the level of activity of the active ingredient, and the habits and practices as established via testing or those which are long accepted in medical practice.

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Method of Use

The present invention also relates to a method for controlling the level of one or more inflammation inducing cytokines, inter alia, interleukin-1 (IL-1), Tumor Necrosis Factor-α (TNF-α), interleukin-6 (IL-6), and interleukin-8 (IL-8) and thereby controlling, mediating, or abating disease states affected by the levels of extracellular inflammatory cytokines. The present method comprises the step of administering to a human or higher mammal an effective amount of a composition comprising one or more of the inflammatory cytokine inhibitors according to the present invention.

Because the inflammatory cytokine inhibitors of the present invention can be delivered in a manner wherein more than one site of control can be achieved, more than one disease state can be modulated at the same time. Non-limiting examples of diseases which are affected by control or inhibition of inflammatory cytokine inhibitors, thereby modulating excessive cytokine activity, include osteoarthritis, rheumatoid arthritis, diabetes, human Immunodeficiency virus (HIV) infection.

In addition, it has now been surprisingly discovered that the analogs (compounds) of the present invention are capable of providing analgesia in humans and higher mammals. As such, the present invention relates to a method for providing analgesia and/or pain relief to humans or higher mammals which comprises the step of administering to said human or higher mammal an effective amount of a 6,7-dihydro-5H-pyrazolo[1,2α]pyrazol-1-one described herein above.

The present invention further comprises a method for providing analgesia and/or pain relief to humans or higher mammals which comprises the step of administering to said human or higher mammal a pharmaceutical composition which comprises:

a) an effective amount of one or more 6,7-dihydro-5H-pyrazolo[1,2α]pyrazol-1-ones and derivatives thereof according to the present invention which are effective for inhibiting release of inflammatory cytokines;

b) an effective amount of one or more compounds having pain relief properties; and c) one or more pharmaceutically acceptable excipients.

The third aspect of methods of the present invention relates to reducing psoriasis in humans and higher mammals, said method comprising the step of administering to a human or high mammal an effective amount of a 6,7-dihydro-5H-pyrazolo[1,2α]pyrazol-1-one according to the present invention. It is well established that the control of cytokine activity is directly related to the formation of psoriasis and inhibition of this activity can be used as a therapy to control this condition. For example, see:

Lamotalos J., et al., "Novel Biological Immunotherapies for Psoriasis." *Expert Opinion Investigative Drugs*; (2003); 12, 1111-1121.

The present invention comprises a method for controlling the extracellular release of cycloxygenase-2 (COX-2) cytokines in human and higher mammals, said method comprising the step of administering to said humans or higher mammals one or more 6,7-dihydro-5H-pyrazolo[1,2α]pyrazol-1-ones and derivatives thereof according to the present invention.

The present invention comprises a method for controlling the extracellular release of Tumor Necrosis Factor-α (TNF-α), in human and higher mammals, said method comprising the step of administering to said humans or higher mammals one or more 6,7-dihydro-5H-pyrazolo[1,2α]pyrazol-1-ones and derivatives thereof according to the present invention.

The present invention comprises a method for controlling a disease or disease state in humans or higher mammals, said disease or disease state chosen from congestive heart failure; hypertension; chronic obstructive pulmonary disease (COPD) and septic shock syndrome; tuberculosis, adult respiratory distress, and asthma; atherosclerosis; muscle degeneration and periodontal disease; cachexia, Reiter's syndrome, gout, acute synovitis, anorexia, bulimia nervosa; fever, malaise, myalgia and headaches, said method comprising the step of administering to said humans or higher mammals one or more 6,7-dihydro-5H-pyrazolo[1,2α]pyrazol-1-ones and derivatives thereof according to the present invention.

The present invention comprises a method for preventing elevated plasma levels of inflammatory cytokines in humans and higher mammals wherein said cytokines are chosen from TNF-α, IL-1β, and IL-6, thereby controlling or treating congestive heart failure in humans and higher mammals, said method comprising the step of administering to said humans or higher mammals one or more 6,7-dihydro-5H-pyrazolo[1,2α]pyrazol-1-ones and derivatives thereof according to the present invention.

The present invention comprises a method for treating Crohn's disease or alleviating the symptoms thereof in humans by controlling the extracellular release of cytokines, said method comprising the step of administering to said humans one or more 6,7-dihydro-5H-pyrazolo[1,2α]pyrazol-1-ones and derivatives thereof according to the present invention.

The present invention also comprises a method for treating psoriasis in humans which comprises the step of administering to said human a pharmaceutical composition which comprises:

a) an effective amount of one or more 6,7-dihydro-5H-pyrazolo[1,2α]pyrazol-1-ones and derivatives thereof according to the present invention which are effective for inhibiting and/or controlling the release of inflammatory cytokines and thereby controlling psoriasis; and b) one or more pharmaceutically acceptable excipients.

For the purposes of the present invention the term "an effective amount" as it relates to the amount of one or more 6,7-dihydro-5H-pyrazolo[1,2α]pyrazol-1-ones delivered to a patient in need of treatment, is defined herein as, "an amount of a pharmaceutically active compound which produces the alleviation of symptoms or the suppression of cytokine activity as measured directly, for example, by a laboratory test or procedure, or indirectly, for example, by the ability of the patient not to experience undesirable disease or disease state symptoms." Said symptoms are necessarily dependent upon one or more factors, inter alia, level of cytokine activity, age of the patient, degree of disease involvement, other diseases or disease states present, desired outcome (complete cure as in a chronic illness or temporary relief as in an acute illness condition). It is recognized that the compositions of the present invention can be delivered in various dosages and therefore, the effective amount can be determined on a patient by patient basis if necessary.

Procedures

The compounds of the present invention can be evaluated for efficacy, for example, measurements of cytokine inhibition constants, $K_i$, and $IC_{50}$ values can be obtained by any method chosen by the formulator.

Non-limiting examples of suitable assays include:
i) UV-visible substrate enzyme assay as described by L. Al Reiter, *Int. J. Peptide Protein Res.*, 43, 87-96 (1994).
ii) Fluorescent substrate enzyme assay as described by Thornberry et al., *Nature*, 356, 768-774 (1992).
iii) PBMC Cell assay as described in U.S. Pat. No. 6,204,261 B1 Batchelor et al., issued Mar. 20, 2001.

Each of the above citations is included herein by reference.

In addition, Tumor Necrosis Factor, TNF-α, inhibition can be measured by utilizing lipopolysaccharide (LPS) stimulated human monocytic cells (THP-1) as described in:
i) K. M. Mohler et al., "Protection Against a Lethal Dose of Endotoxin by an Inhibitor of Tumour Necrosis Factor Processing", *Nature*, 370, pp 218-220 (1994).
ii) U.S. Pat. No. 6,297,381 B1 Cirillo et al., issued Oct. 2, 2001, incorporated by reference and reproduced herein below in relevant portion thereof.

The inhibition of cytokine production can be observed by measuring inhibition of TNF-α in lipopolysaccharide stimulated THP cells. All cells and reagents are diluted in RPMI 1640 with phenol red and L-glutamine, supplemented with additional L-glutamine (total: 4 mM), penicillin and streptomycin (50 units/mL each) and fetal bovine serum (FBS 3%) (GIBCO, all conc. Final). Assay is performed under sterile conditions, only test compound preparation is non-sterile. Initial stock solutions are made in DMSO followed by dilution into RPMI 1640 2-fold higher than the desired final assay concentration. Confluent THP. 1 cells ($2\times10^6$ cells/mL, final conc.; American Type Culture Company, Rockville, Md.) are added to 96 well polypropylene round bottomed culture plates (Costar 3790; sterile) containing 125 µL test compound (2-fold concentrated) or DMSO vehicle (controls, blanks). DMSO concentration should not exceed 0.2% final. Cell mixture is allowed to preincubate for 30 minutes at 37° C., 5% $CO_2$ prior to stimulation with lipopolysaccharide (LPS, 1 µg/mL final; Sigma L-2630, from *E. coli* serotype 0111.B4; stored as 1 mg/mL stock in endotoxin screened diluted $H_2O$ vehicle at −80° C.). Blanks (unstimulated) receive $H_2O$ vehicle; final incubation volume is 250 µL. Incubation (4 hours) proceeds as described above. Assay is to be terminated by centrifuging plates 5 minutes at room temperature, 1600 rpm (4033 g); supernatants are then transferred to clean 96 well plates and stored at −80° C. until analyzed for human TNF-α by a commercially available ELISA kit (Biosource #KHC3015, Camarillo, Calif.). The calculated $IC_{50}$ value is the concentration of the test compound that caused a 50% decrease in the maximal TNF-α production.

The compounds of the present invention have been found to be surprisingly effective in providing analgesia, or otherwise relieving pain in humans and higher mammals. One convenient means for evaluating pain and for measuring the effective amount of compound(s) necessary to achieve analgesia and, therefore, provide a means for determining the amount of compound(s) which comprises a pharmaceutical composition of the present invention and the amount of compound(s) necessary for use in the methods described herein, is the Rat Thermal Hyperalgesia Model as described herein below.

The Rat Thermal Hyperalgesia Model, i.e., "Hargreaves Method" [Hargreaves, K., et al., *Pain*, (1988), 32:77-88], is used to determine the level at which the systemic administration of test compounds attenuate the hyperalgesia response subsequent to an intraplantar injection of carrageenan.

Analgesia Test Method:

Sprague-Dawley male rats weighing 100-150 g and housed two per shoebox cage in sanitary, ventilated animal rooms with controlled temperature, humidity and regular light cycles are used. Rodent chow and water were allowed ad libitum. Animals are acclimated for one week before use. All animal use is in accordance with the United States Department of Agriculture guidelines for humane care.

On the first day of study, each animal is acclimated to test equipment and the baseline paw withdrawal latency (PWL) to a radiant heat source is recorded. The following day, animals are orally dosed with vehicle or test compound. Thirty minutes later, each animal receives a 0.1 mL intra plantar injection of carrageenan (1.2% solution, w/v) into the left hind paw. Four hours post-carrageenan injection, animals are returned to the test equipment to determine PWL of the inflamed paw. The animals are then humanely euthanized with an overdose of carbon dioxide.

Statistical analysis of data: Change from pre to post PWL for each animal is calculated. Statistical comparison between treatment groups on these two end points are made via an ANCOVA model with treatment terms, as well as pre-treatment measure as baseline covariate.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound or enantiomeric and diasteriomeric forms or pharmaceutically acceptable salts thereof, said compound having the formula:

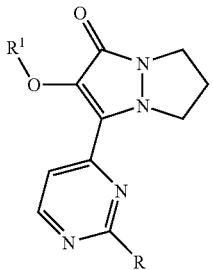

wherein R is:
a) —O[CH$_2$]$_k$R$^3$; or
b) —NR$^{4a}$R$^{4b}$;
R$^3$ is substituted or unsubstituted C$_1$-C$_4$ alkyl, substituted or unsubstituted carbocyclic, substituted or unsubstituted heterocyclic, substituted or unsubstituted aryl or alkylenearyl, substituted or unsubstituted heteroaryl or alkyleneheteroaryl;
the index k is from 0 to 5;
R$^{4a}$ and R$^{4b}$ are each, independently:
a) hydrogen; or
b) —[C(R$^{5a}$R$^{5b}$)]$_m$R$^6$;
R$^{5a}$ and R$^{5b}$ are each; independently, hydrogen, —OR$^7$, —N(R$^7$)$_2$, —CO$_2$R$^7$, —CON(R$^7$)$_2$; C$_1$-C$_4$ liner, branched, or cyclic alkyl; R$^6$ is hydrogen, —OR$^7$, —N(R$^7$)$_2$, —CO$_2$R$^7$, —CON(R$^7$)$_2$; substituted or unsubstituted C$_1$-C$_4$ alkyl, substituted or unsubstituted heterocyclic, substituted or unsubstituted aryl, or substituted or unsubstituted heteroaryl; R$^7$ is hydrogen, C$_1$-C$_4$ alkyl, or substituted or unsubstituted aryl; the index m is from 0 to 5;
and wherein R$^1$ is:
a) substituted or unsubstituted aryl; or
b) substituted or unsubstituted heteroaryl.

2. A compound according to claim 1 wherein R is a unit having the formula —OR$^3$ and R$^3$ is substituted or unsubstituted aryl.

3. A compound according to claim 2 wherein R$^3$ is chosen from phenyl, 2-fluorophenyl, 3-fluorophenyl, 4-fluorophenyl, 2,4-difluorophenyl, 3-trifluoromethylphenyl, 4-trifluoromethylphenyl, 2,4-trifluoromethyl phenyl, 2 methylphenyl, 3-methyl-phenyl, 4-methylphenyl, 2,4-dimethylphenyl, 2-cyanophenyl, 3-cyanophenyl, 4-cyanophenyl, 4-ethylphenyl, (2-methyoxy)phenyl, (3-methyoxy)phenyl, (4-methoxy) phenyl, and 3-[(N-acetyl)amino)phenyl, and benzo[1,3]dioxol-5-yl.

4. A compound according to claim 1 wherein R is a unit having the formula —OR$^3$ and R$^3$ is chosen from pyrimidin-2-yl, pyrimidin-4-yl, pyridin-2-yl, pyridin-3-yl, pyridin-4-yl, 2-aminopyrimidin-4-yl.

5. A compound according to claim 1 wherein R is a unit having the formula —OR$^3$ and R$^3$ is substituted or unsubstituted C$_1$-C$_4$ linear or, branched alkyl, or substituted or unsubstituted carbocyclic.

6. A compound according to claim 5 wherein R$^3$ is chosen from 2-methoxyethyl, or (S)-1-methyl-3-methoxypropyl.

7. A compound according to claim 1 wherein R is a unit having the formula:

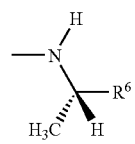

wherein R$^6$ is substituted or unsubstituted phenyl.

8. A compound according to claim 7 wherein R is chosen from (S)-1-methyl-1-phenylmethylamino, (S)-1-methyl-1-(4-fluorophenyl)methylamino, (S)-1-methyl-1-(4-methylphenyl)methyl-amino, (S)-1-methyl-1-(4-methoxyphenyl) methylamino, (S)-1-methyl-1-(2-aminophenyl) methylamino, and (S)-1-methyl-1-(4-aminophenyl)methylamino.

9. A compound according to claim 1 wherein R is chosen from (S)-1-methyl-1-(pyridin-2-yl)methylamino, (S)-1-methyl-1-(pyridin-3-yl)methylamino, (S)-1-methyl-1-(pyridin-4-yl)methylamino, (S)-1-methyl-1-(furan-2-yl)methylamino, and (S)-1-methyl-1-(benzo[1,3]dioxol-5-yl) methylamino.

10. A compound according to claim 1 wherein R is chosen from (S)-1-methylpropylamine or (S)-1-methyl-2-(methoxy) ethylamino.

11. A compound according to claim 1 wherein R has the formula:

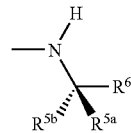

and the indicated stereochemistry when R$^{5a}$, R$^{5b}$ and R$^6$ are not the same.

12. A compound according to claim 11 wherein R is chosen from 1,1-dimethylethylamine, 1,1-dimethylbenzylamine, (S)-1-methyl-2-hydroxy-2-methylpropylamine, (S)-1-methyl-2-hydroxy-2-methylbutylamine, benzylamino, (2-aminophenyl)methylamino; (4-fluorophenyl)methylamino, (4-methoxyphenyl)methylamino; (4-propanesulfonyl-phenyl)methylamino, (2-methylphenyl)methylamino; (3-methylphenyl)-methylamino; and (4-methylphenyl)methylamino.

13. A compound or enantiomeric and diasteriomeric forms or pharmaceutically acceptable salts thereof, said compound having the formula:

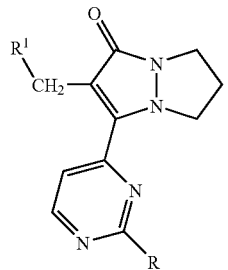

wherein R is:
a) —O[CH$_2$]$_k$R$^3$; or
b) —NR$^{4a}$R$^{4b}$;

R$^3$ is substituted or unsubstituted C$_1$-C$_4$ alkyl, substituted or unsubstituted carbocyclic, substituted or unsubstituted heterocyclic, substituted or unsubstituted aryl or alkylenearyl, substituted or unsubstituted heteroaryl or alkyleneheteroaryl;

the index k is from 0 to 5;

R$^{4a}$ and R$^{4b}$ are each, independently:

a) hydrogen; or
b) —[C(R$^{5a}$R$^{5b}$)]$_m$R$^6$;

R$^{5a}$ and R$^{5b}$ are each; independently, hydrogen, —OR$^7$, —N(R$^7$)$_2$, —CO$_2$R$^7$, —CON(R$^7$)$_2$; C$_1$-C$_4$ liner, branched, or cyclic alkyl; R$^6$ is hydrogen, —OR$^7$, —N(R$^7$)$_2$, —CO$_2$R$^7$, —CON(R$^7$)$_2$; substituted or unsubstituted C$_1$-C$_4$ alkyl, substituted or unsubstituted heterocyclic, substituted or unsubstituted aryl, or substituted or unsubstituted heteroaryl; R$^7$ is hydrogen, C$_1$-C$_4$alkyl, or substituted or unsubstituted aryl; the index m is from 0 to 5;

and wherein R$^1$ is:
a) substituted or unsubstituted aryl; or
b) substituted or unsubstituted heteroaryl.

14. A compound according to claim 13 wherein R is a unit having the formula —OR$^3$ and R$^3$ is substituted or unsubstituted aryl.

15. A compound according to claim 14 wherein R$^3$ is chosen from phenyl, 2-fluorophenyl, 3-fluorophenyl, 4-fluorophenyl, 2,4-difluorophenyl, 3-trifluoromethylphenyl, 4-trifluoromethylphenyl, 2,4-trifluoromethylphenyl, 2-methylphenyl, 3 methyl-phenyl, 4-methylphenyl, 2,4-dimethylphenyl, 2-cyanophenyl, 3-cyanophenyl, 4-cyanophenyl, 4-ethylphenyl, (2-methyoxy)phenyl, (3-methyoxy)phenyl, (4-methoxy)phenyl, 3-[(N-acetyl)amino]phenyl, and 3-benzo[1,3]dioxol-5-yl.

16. A compound according to claim 13 wherein R is a unit having the formula —OR$^3$ and R$^3$ is chosen from pyrimidin-2-yl, pyrimidin-4-yl, pyridin-2-yl, pyridin-3-yl, pyridin-4-yl, 2-aminopyrimidin-4-yl.

17. A compound according to claim 13 wherein R is a unit having the formula —OR$^3$ and R$^3$ is substituted or unsubstituted C$_1$-C$_4$ linear or branched alkyl, or substituted or unsubstituted carbocyclic.

18. A compound according to claim 17 wherein R$^3$ is chosen from 2-methoxyethyl, or (S)-1-methyl-3-methoxypropyl.

19. A compound according to claim 13 wherein R is a unit having the formula:

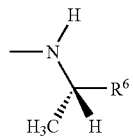

wherein R$^6$ is substituted or unsubstituted phenyl.

20. A compound according to claim 19 wherein R is chosen from (S)-1-methyl-1-phenylmethylamino, (S)-1-methyl-1-(4-fluorophenyl)methylamino, (S)-1-methyl-1-(4-methylphenyl)methyl-amino, (S)-1-methyl-1-(4-methoxyphenyl) methylamino, (S)-1-methyl-1-(2-aminophenyl) methylamino, and (S)-1-methyl-1-(4-aminophenyl)methyl-amino.

21. A compound according to claim 13 wherein R is chosen from (S)-1-methyl-1-(pyridin-2-yl)methylamino, (S)-1-methyl-1-(pyridin-3-yl)methylamino, (S)-1-methyl-1-(pyridin-4-yl)methylamino, (S)-1-methyl-1-(furan-2-yl)methylamino, and (S)-1-methyl-1-(benzo[1,3]dioxol-5-yl) methylamino.

22. A compound according to claim 13 wherein R is chosen from (S)-1-methylpropylamino or (S)-1-methyl-2-(methoxy) ethylamino.

23. A compound according to claim 13 wherein R has the formula:

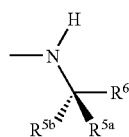

and the indicated stereochemistry when R$^{5a}$, R$^{5b}$ and R$^6$ are not the same.

24. A compound according to claim 23 wherein R is chosen from 1,1-dimethylethylamine, 1,1-dimethylbenzylamine, (S)-1-methyl-2-hydroxy-2-methylpropylamine, (S)-1-methyl-2-hydroxy-2-methylbutylamine, benzylamino, (2-aminophenyl)methylamino; (4-fluorophenyl)methylamino, (4-methoxyphenyl)methylamino; (4-propanesulfonyl-phenyl)methylamino, (2-methylphenyl)methylamino; (3-methylphenyl)-methylamino; and (4-methylphenyl)methylamino.

25. A compound or enantiomeric and diasteriomeric forms or pharmaceutically acceptable salts thereof, said compound having the formula:

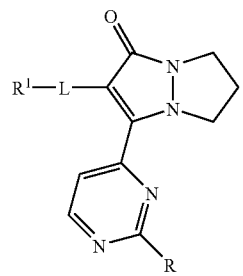

wherein L is chosen from —CH$_2$NHC(O)—, —NHC(O)—, and —C(O)—and wherein R is:
a) —O[CH$_2$]$_k$R$^3$; or
b) —NR$^{4a}$R$^{4b}$;

R³ is substituted or unsubstituted $C_1$-$C_4$ alkyl, substituted or unsubstituted carbocyclic, substituted or unsubstituted heterocyclic, substituted or unsubstituted aryl or alkylenearyl, substituted or unsubstituted heteroaryl or alkyleneheteroaryl;

the index k is from 0 to 5;

$R^{4a}$ and $R^{4b}$ are each, independently:
a) hydrogen; or
b) —$[C(R^{5a}R^{5b})]_m R^6$;

$R^{5a}$ and $R^{5b}$ are each; independently, hydrogen, —$OR^7$, —$N(R^7)_2$, —$CO_2R^7$, —$CON(R^7)_2$; $C_1$-$C_4$ liner, branched, or cyclic alkyl; $R^6$ is hydrogen, —$OR^7$, —$N(R^7)_2$, —$CO_2R^7$, —$CON(R^7)_2$; substituted or unsubstituted $C_1$-$C_4$ alkyl, substituted or unsubstituted heterocyclic, substituted or unsubstituted aryl, or substituted or unsubstituted heteroaryl; $R^7$ is hydrogen, $C_1$-$C_4$alkyl, or substituted or unsubstituted aryl; the index m is from 0 to 5;

and wherein $R^1$ is:
a) substituted or unsubstituted aryl; or
b) substituted or unsubstituted heteroaryl.

26. A compound chosen from:
(S)-3-[2-(2-Methoxy-1-methyl-ethylamino)-pyrimidin-4-yl]2-o-tolyoxy-6,7-dihydro-5H-pyrazolo[1,2-a]pyrazol-1-one;
(S)-3-[2-(2-Hydroxy-1,2-dimethyl-propylamino)-pyrimidin-4-yl]-2-o-tolyloxy-6,7-dihydro-5H-pyrazolo[1,2-a]pyrazol-1-one;
(S)-3-[2-(Tetrahydro-pyran-4-ylamino)-pyrimidin-4-yl]-2-o-tolyloxy-6,7-dihydro-5H-pyrazolo[1,2-a]pyrazol-1-one;
(S)-3-[2-(1-Phenyl-ethylamino)-pyrimidin-4-yl]-2-o-tolyloxy-6,7-dihydro-5H-pyrazolo[1,2-a]pyrazol-1-one;
3-[2(2,6-Dichloro-phenylamino)-pyrimidin-4-yl]-2-o-toxyloxy-6,7-dihydro-5H-pyrazolo[1,2-a]pyrazol-1-one;
3-(2-Phenoxy-pyrimidin-4-yl)-2-o-tolyloxy-6,7-dihydro-5H-pyrazolo[1,2-a]pyrazol-1-one;
(S)-2-(2-Chlorobenzyl)-3-[2-(1-phenyl-ethylamino)-pyrimidin-4-yl]-6,7-dihydro-5H-pyrazolo[1,2-a]pyrazol-1-one;
(S)-2-(2-Methyl-benzyl)-3-[2-(1-phenyl-ethylamino)-pyrimidin-4-yl]-6,7-dihydro-5H-pyrazolo[1,2-a]pyrazol-1-one;
(S)-2-(4-Fluorobenzyl)-3-[2-(1-phenyl-ethylamino)-pyrimidin-4-yl]-6,7-dihydro-5H-pyrazolo[1,2-a]pyrazol-1-one;
2-(2-Chlorobenzyl)-3-[2-(2,6-difluoro-phenylamino)-pyrimidin-4-yl]-6,7-dihydro-5H-pyrazolo[1,2-a]pyrazol-1-one;
(S)-2-(2-Chlorobenzyl)-3-[2-(2-hydroxy-1,2-dimethyl-propylamino)-pyrimidin-4-yl]-6,7-dihydro-5H-pyrazolo[1,2-a]pyrazol-1-one;
(S)-3-[2-(2-Hydroxy-1,2-dimethyl-propylamino)-pyrimidin-4-yl]-2-(2-methyl-benzyl)-6,7-dihydro-5H-pyrazolo[1,2-a]pyrazol-1-one;
(S)-2-(4-Fluorobenzyl)-3-[2-(2-hydroxy-1,2-dimethyl-propylamino)-pyrimidin-4-yl]-6,7-dihydro-5H-pyrazolo[1,2-a]pyrazol-1-one;
2-(2-Chlorobenzyl)-3-[2-(tetrahydro-pyran-4-ylamino)-pyrimidin-4-yl]-6,7-dihydro-5H-pyrazolo[1,2-a]pyrazol-1-one;
2-(2-Chlorobenzyl)-3-(2-phenoxy-pyrimidin-4-yl)-6,7-dihydro-5H-pyrazolo[1,2-a]pyrazol-1-one;
1-Oxo-3-(2-phenoxy-pyrimidin-4-yl)-6,7-dihydro-1H,5H-pyrazolo[1,2-a]pyrazole-2-carboxylic acid 2-chloro-benzylamide;
1-Oxo-3-(2-phenoxy-pyrimidin-4-yl)-6,7-dihydro-1H,5H-pyrazolo[1,2-a]pyrazole-2-carboxylic acid (2-chloro-phenyl)-amide;
2-(2-Chloro-benzyl)-3-[2-(2-methoxy-1-methyl-ethylamino)-pyrimidin-4-yl]-6,7-dihydro-5H-pyrazolo[1,2-a]pyrazol-1-one;
2-(2-Chlorobenzoyl)-3-(2-phenoxy-pyrimidin-4-yl)-6,7-dihydro-5H-pyrazolo[1,2-a]pyrazol-1-one; and
2-(2-Chloro-benzyl)-3-[2-(2-methoxy-1-methyl-ethylamino)-pyrimidin-4-yl]-6,7-dihydro-5H-pyrazolo[1,2-a]pyrazol-1-one.

27. A method of treating a condition selected from the group consisting of osteoarthritis, rheumatoid arthritis, or the combination thereof, comprising administering to a mammal in need of such treatment a pharmaceutical composition comprising the compound according to claim 1.

28. A method of treating a condition selected from the group consisting of osteoarthritis, rheumatoid arthritis, or the combination thereof, comprising administering to a mammal in need of such treatment a pharmaceutical composition comprising the compound according to claim 13.

29. A method of treating a condition selected from the group consisting of osteoarthritis, rheumatoid arthritis, or the combination thereof, comprising administering to a mammal in need of such treatment a pharmaceutical composition comprising the compound according to claim 25.

* * * * *